United States Patent [19]
Yamagata

[11] Patent Number: 5,823,998
[45] Date of Patent: Oct. 20, 1998

[54] INJECTION APPARATUS

[75] Inventor: Hideto Yamagata, Saitama, Japan

[73] Assignee: Eli Lilly Japan Kabushiki Kaisha, Hyogo, Japan

[21] Appl. No.: 793,190
[22] PCT Filed: Aug. 23, 1995
[86] PCT No.: PCT/JP95/01661
    § 371 Date: Feb. 20, 1997
    § 102(e) Date: Feb. 20, 1997
[87] PCT Pub. No.: WO96/05878
    PCT Pub. Date: Feb. 29, 1996

[30] Foreign Application Priority Data

Aug. 24, 1994 [JP] Japan .................................. 6-199494

[51] Int. Cl.$^6$ .................................................. A61M 5/20
[52] U.S. Cl. ........................................ 604/131; 604/181
[58] Field of Search .................... 604/167, 131, 604/164, 181

[56] References Cited

U.S. PATENT DOCUMENTS

| | | | |
|---|---|---|---|
| 4,627,835 | 12/1986 | Fenton, Jr. | 604/67 |
| 4,952,205 | 8/1990 | Mauerer et al. | 604/67 |
| 5,242,408 | 9/1993 | Jhuboo et al. | 604/67 X |
| 5,378,231 | 1/1995 | Johnson et al. | 604/67 |
| 5,545,140 | 8/1996 | Conero et al. | 604/67 X |
| 5,611,784 | 3/1997 | Barresi et al. | 604/67 X |

FOREIGN PATENT DOCUMENTS

| | | |
|---|---|---|
| 0 337 252 A | 10/1989 | European Pat. Off. . |
| 87 14 553 U | 4/1988 | Germany . |
| 741 604 | 12/1955 | United Kingdom . |
| WO 86/00815 | 7/1985 | WIPO . |
| WO 87/07843 | 6/1987 | WIPO . |

*Primary Examiner*—Max Hindenburg
*Attorney, Agent, or Firm*—Douglas J. Taylor; David E. Boone

[57] ABSTRACT

In an injection apparatus, a guide screw shaft of a body section (20) and a screw of an operation knob (34) of a movable section (30) allow the movable section (30) to move relative to the body section (20). An ampule (7) is radially inserted into a ampule holding portion (36) of the movable section (30) and temporarily held by means of an elastic blade (36a) and at the same time, a flange (75) of the ampule (70) is inserted into a flange insertion portion (38). When the operation knob (34) is rotated, the movable section (30) moves toward the body section (20) together with the ampule (70). A guide sleeve formed in the body section (20) is inserted into a syringe (77) of the ampule (70). An operation knob (50) is rotated to set the feeding amount of a piston rod, and the operation knob (50) is pressed to perform an injection. When a release button (40) is pressed, the piston rod is returned to an initial position. This construction allows the ampule (70) to be easily mounted on the injection apparatus and the state of medicine in the ampule (70) to be easily seen.

21 Claims, 19 Drawing Sheets

INJECTION APPARATUS

TECHNICAL FIELD

The present invention relates to an injection apparatus, particularly to the injection apparatus, having an ampule mounted thereon, for manually giving an injection of a medicine in the ampule to a patient, and more particularly to the injection apparatus which is suitable for an ampule containing two-component medicine.

BACKGROUND ART

As an injection apparatus, for giving an injection of a medicine (agent) in an ampule, which is prepared by installing the ampule thereon and mounting a needle on the ampule, and which is operated to inject the medicine in the ampule, a pen-type of injection apparatus as shown in FIG. 1 generally, is mainly used. The injection apparatus 90 of this type comprises a cylindrical body 92 and a cap 94, and an ampule 95 is inserted into the body 92. A needle 91 is mounted on a front end of the ampule 95 projecting from an end of the body 92. Then, a knob 96 positioned at a rear end of the cap 94 is operated to set an injection amount. Then, the knob 96 is pushed toward the needle 91 to move a piston 99 of the ampule 95 through a rod 97. In this manner, a medicine 98 is injected to a patient.

In this type of injection apparatus, however, for the installation and removal of the ampule 95, it is necessary to remove the cap 94 from the body 92, to insert the ampule 95 into the body 92 or to remove it therefrom, and, then, to install the cap 94 on the body 92 again. It takes time and labor to carry out such an operation, because the engagement between the body 92 and the cap 94 cannot be made favorably or the cap 94 is separated from the body 92. Thus, the injection apparatus has a problem in that an operator is inconvenienced when handling it.

Further, because the entire ampule 95 is hidden in the injection apparatus 90, the ampule 95 is not seen from outside or is hard to see even though the body 92 has a peep window. Thus, there is a problem in that the amount of the medicine 98 is hard to see.

DISCLOSURE OF THE INVENTION

The present invention has been developed in view of the above-described problems. That is, as a first technical problem to be solved by the present invention, the present invention is intended to provide an injection apparatus on which an ampule can be easily mounted. As a second technical problem to be solved by the present invention, the present invention is intended to allow an ampule installed in the injection apparatus to be seen easily from outside. In order to solve the above-described technical problems, the injection apparatus of the present invention is constructed as follows.

That is, the injection apparatus, on which an ample having a piston for sealing an agent in a syringe is installed, has piston rod means for pressing the piston of the ampule in an axial direction. The injection apparatus comprises an ampule holding part and an ampule gripping means. The ampule holding part defines an ampule insertion outer opening which is expanded in a circumferential direction when the ampule is inserted into the opening, and defines an ampule insertion space for inserting the ampule thereinto. In this construction, the outer opening is restored to its original configuration after the ampule is inserted into the ampule insertion space, so that the ampule is held by the ampule holding part temporarily. The ampule gripping means grips the ampule and blocks the movement thereof in both the axial direction and the direction perpendicular to the axis of the ampule.

In the above construction, in order to mount the ampule on the injection apparatus, the ampule is inserted into the ampule insertion space through the opening of the injection apparatus in the axial direction (hereinafter, referred to as an "axis") of the ampule or a direction perpendicular thereto. At this time, the opening is expanded by the ampule. Because the expanded opening is returned to its original configuration after the ampule is inserted into the ampule insertion space, the ampule is prevented from falling out of the ampule insertion space. In other words, the ampule is temporarily held by the ampule-holding part. The ampule-gripping means prevents the ampule temporarily held by the ampule-holding part from moving in both the axial direction and the direction perpendicular to the axis of the ampule. That is, it is unnecessary to disassemble the injection apparatus or the like upon inserting the ampule into the ampule insertion space. The ampule can be mounted on the injection apparatus by inserting the ampule into the ampule insertion space of the ampule-holding part and by fixing it by the ampule-gripping means. Because the ampule is temporarily held thereby, it is unnecessary to take particular care of preventing the ampule from falling out of the injection apparatus.

Accordingly, the ampule with the above construction is easily mounted on the injection apparatus.

Also, the above-described construction allows the inserted ampule to be viewed easily from outside through the outer opening.

Accordingly, the injection apparatus having the above-described construction allows the mounted ampule to be easily seen from outside.

Preferably, the ampule holding part has a pair of ampule-gripping elastic blades for securing the inserted ampule therebetween. The opening is defined between the side edges of the pair of ampule-gripping elastic blades and between the front edges thereof, and the ampule insertion space is defined by an inner peripheral surface of the pair of ampule-gripping elastic blades. The distance between the side edges of the pair of ampule-gripping elastic blades is shorter than an outer diameter of the syringe of the ampule by a predetermined amount.

In the above-described construction, the ampule is inserted into the ampule insertion space through the opening formed between the side edges of the ampule-holding part in a direction perpendicular to the axis. After the ampule is inserted into the ampule insertion space, a front end of the ampule on which a needle unit is installed projects to the outside through the opening formed between the side edges of the ampule-holding part. Because the distance between the side edges of the pair of ampule-gripping elastic blades is shorter than the outer diameter of the syringe of the ampule, the ampule is inserted into the ampule insertion space by expanding the ampule-gripping elastic blades outward. After insertion, the expanded side edges of the ampule-gripping elastic blades are restored to the original configuration. Thus, the movement of the ampule in the direction perpendicular to the axis thereof is elastically limited. Accordingly, the ampule is held in the ampule insertion space temporarily; hence, an accident, such as a dropping or falling of the ampule therefrom at time of ampule-mounting operation, can be prevented.

Preferably, the injection apparatus comprises a body section having a piston rod means and a movable section having an ampule holding part. The body section and the movable section have driving means that allows the body section and the movable section to move relative to each other between an ampule insertion position at which the ampule is inserted into the ampule holding part of the movable section and a setting position at which the movable section is closest to the body section.

In the above-described construction, when the body section and the movable section are placed at the ampule insertion position, the ampule is inserted into the ampule insertion space. At this time, the inserted ampule can be held removably temporarily. When the body section and the movable section are placed at the setting position by the driving means, the ampule can be fixedly held.

With the above-described construction, it is unnecessary to disassemble the injection apparatus. Thus, the ampule can be mounted on the injection apparatus easily.

Preferably, the driving means comprises screw feeding means. The screw feeding means has a guide screw shaft located on the body section and a nut-type operation knob mounted on the movable section such that the operation knob is unmovable in the axial direction thereof, rotatable, and screws on a periphery of the guide screw shaft.

With the above-described construction, the nut-type operation knob screws on the periphery of the guide screw shaft. Thus, when the nut-type operation knob is rotated, the nut-type operation knob moves along the guide screw shaft together with the movable section. That is, with the above-described construction, the movable section and the body section can be moved relative to each other. This construction is particularly advantageous when the ampule contains two components of medicine (agent) and it is necessary to press the piston carefully in order to mix them with each other slowly. In such a case, the nut-shaped operation knob and the screw part of the guide screw shaft may be appropriately selected and constructed to allow the movable section and the body section to move slowly relative to each other when rotating the nut-shaped operation knob without taking particular care.

Preferably, the ampule has a flange, and the ampule-gripping means comprises a flange hold-down part and a flange pressing part The flange hold-down part is formed at a predetermined position of the ampule insertion space of the movable section, contacts a front surface of the flange of the inserted ampule, and moves the ampule rearward by pressing the front surface of the flange of the ampule when the movable section moves to the setting position. The flange pressing part is provided on the body section around the piston rod means and is pressed against a rear surface of the flange of the ampule when the movable section and the body section are placed at the setting position.

With the above-described construction, when the ampule is inserted into the ampule insertion space and when the movable section and the body section are positioned at the setting position, the flange of the ampule is sandwiched between the flange hold-down part and the flange pressing part with the front surface of the flange in contact with the flange hold-down part and the rear surface thereof in contact with the flange pressing part. That is, the movement of the ampule is fixed in its axial direction.

Preferably, the flange pressing part comprises a spacer and an elastic O-ring. The spacer freely engages the periphery of the piston rod means and is placed at a predetermined position of the ampule insertion space when the movable section is located at the ampule insertion position so that the spacer substantially contacts the rear surface of the flange of the ampule. The elastic O-ring is provided at a predetermined position of the periphery of the piston rod means such that the elastic O-ring is axially unmovable and pressed against a rear surface of the spacer when the movable section is located at the setting position.

In the above-described construction, the flange of the ampule presses the spacer rearward along the guide sleeve. When the movable section reaches the setting position, one surface of the spacer contacts the rear surface of the flange of the ampule with the outer surface of the spacer being pressed by the elastic O-ring. Accordingly, the flange of the ampule is fixed axially through the spacer by the elastic force of the elastic O-ring without a backlash.

Preferably, the piston rod means comprises a guide sleeve, a piston rod, and a screw rod. The guide sleeve is fixed to the body section, projects forward from the body section, is concentric with the inserted ampule, and has an outer diameter generally equal to an inner diameter of the syringe of the ampule. The piston rod is inserted into the guide sleeve such that the piston rod is nonrotatable with respect to the guide sleeve and axially slidable, and the piston rod has a screw hole. The screw rod has a screw part, formed at a front end thereof, and screwing on a screw part of the screw hole of the piston rod, and has an operation knob formed at a rear end thereof. The screw rod is movable together with the piston rod between an initial position and a pushing-in position.

In the above-described construction, the front end of the screw rod screws on the piston rod and the piston rod does not rotate. Therefore, when the operation knob positioned at the rear end of the screw rod is rotated to rotate the screw rod, the piston rod moves relative to the screw rod. Thus, when the piston rod is moved forward relative to the screw rod at the initial position, and when the screw rod is pushed in up to the pushing-in position, the piston of the ampule is displaced correspondingly. That is, an injection amount can be set which corresponds to the rotation amount of the screw rod. The injection amount can be set at the initial position, and can be set again when the screw rod is returned from the pushing-in position to the initial position.

In the above-described construction, the piston rod moves forward or backward relative to the screw rod, depending upon the rotational direction of the screw rod. In order to set a subsequent injection amount after an injection is given to a patient, it is necessary to feed the piston rod forward relative to the screw rod by rotating the screw rod after the screw rod is returned to the initial position. If the screw rod is rotated reversely to move the piston rod rearward relative to the screw rod, there is a gap formed between the piston rod and the piston of the ampule when the screw rod is pushed in next. As a result, it is not possible to give the injection even though the screw rod is pressed.

Accordingly, preferably, the piston rod means further comprises rotation regulation means for regulating the rotational direction of the screw rod in one direction.

With the above-described construction, the rotational direction of the screw rod is limited to the direction in which the piston rod is moved forward relative to the screw rod. Thus, an erroneous operation in setting the injection amount can be prevented.

Preferably, the injection apparatus further comprises detection means, display means, and rotation regulation release means. The detection means detects the rotational amount of the screw rod of the piston rod means and detects a return of the screw rod from the pushing-in position to the initial position. The display means displays an injection amount which corresponds to the rotational amount of the screw rod of the piston rod means after the screw rod returns to the initial position. The rotation regulation release means releases the rotation regulation means of the piston rod means when the ampule is to be removed from the ampule insertion space.

In the above-described construction, based on signals, outputted from the detection means, which indicate the rotational amount of the screw rod and the return thereof to the initial position, the display means displays an injection amount which corresponds to the amount of the rotation of the screw rod after the return of the screw rod to the initial position. Thus, it is always possible to check the injection amount set.

Further, the rotation regulation release means releases the rotation regulation means of the piston rod means, which allows the piston rod to be moved rearward by rotating the screw rod reversely. Therefore, an inconvenience that the ampule cannot be removed from the ampule insertion space because the piston rod is present in the syringe of the ampule is eliminated.

In the above-described construction, when the screw rod is rotated relative to the piston rod in setting an injection amount, there are two cases, one in which the piston rod moves forward and the other in which the piston rod moves rearward axially relative to the body section of the injection apparatus. When the piston rod moves forward axially, an injection amount can be set by moving the piston rod until the piston rod contacts the piston of the syringe. But if the piston rod is moved further than that, the piston rod presses the piston of the syringe, thus pressing out medicine therefrom. Thus, there is a restriction in the injection amount which can be set. On the other hand, when the screw rod moves rearward axially, there is no such restriction in the injection amount which can be set. The construction in which the screw rod moves rearward axially is described below.

That is, a concave part is formed on a peripheral surface of the piston rod. The concave part comprises a bottom surface generally parallel with an inner peripheral surface of the guide sleeve, a front step surface being provided on a front side of the bottom surface and extending from the bottom surface outwardly in a radial direction of the piston rod, and a rear step surface being provided on a rear side of the bottom surface and extending from the bottom surface outwardly in the radial direction of the piston rod. The concave part may be plural. For example, the concave may be dovetail groove-shaped. That is, the concave may be a long and narrow groove extending axially. The piston rod means further comprises a spring means and a stopper member. The spring means automatically returns the screw rod and the piston rod to the initial position when a force for pushing the screw rod and the piston rod in is released. The stopper member is positioned in the concave of the piston rod, slidably contacts the bottom surface of the piston rod and the inner peripheral surface of the guide sleeve with a predetermined frictional force, moves together with the piston rod with the stopper member in contact with the rear step surface of the piston rod when the piston rod is pushed in, and stops the movement of the piston rod with the stopper member in contact with the front step surface of the piston rod when the piston rod is returned by the spring means. The frictional force between the stopper member and the bottom surface of the piston rod is smaller than the automatic return force of the spring means. The frictional force between the stopper member and the inner peripheral surface of the guide sleeve is greater than the automatic return force of the spring means.

In the above-described construction, the frictional force between the stopper member and the bottom surface of the piston rod is smaller than the automatic return force of the spring means. The frictional force between the stopper member and the inner peripheral surface of the guide sleeve is greater than the automatic return force of the spring means. Therefore, when the screw rod is pressed with a force greater than the frictional force between the stopper member and the inner peripheral surface of the guide sleeve, the stopper member positioned between the piston rod and the guide sleeve is stationary relative to the guide sleeve, and the piston rod moves forward slidably contacting the bottom surface of the guide sleeve. This is because the frictional force between the stopper member and the bottom surface of the piston rod is smaller than the frictional force between the stopper member and the inner peripheral surface of the guide sleeve. When the stopper member is brought into contact with the rear step surface of the piston rod, the stopper member moves, with the stopper member being pressed by the rear step surface of the piston rod. That is, the stopper member slides in contact with the inner peripheral surface of the guide sleeve. When the piston rod is returned by the spring means, the piston rod moves in the return direction until it contacts the front surface of the stopper member because the frictional force between the stopper member and the bottom surface of the piston rod is smaller than the automatic return force of the spring means. That is, the bottom surface of the piston rod and the stopper member slide in contact with each other. When the piston rod contacts the front surface of the stopper member, the stopper member keeps stationary relative to the guide sleeve because the frictional force between the stopper member and the inner peripheral surface of the guide sleeve is greater than the automatic return force of the spring means. Accordingly, the piston rod does not move further and the position of the piston rod becomes the initial position of a subsequent injection. At the initial position, the screw rod is rotated to feed it relative to the piston rod, and then the screw rod is pressed; as a result, the piston of the syringe is pushed out. That is, it is possible to inject an amount of medicine in correspondence to the feeding amount of the screw rod.

Accordingly, in the above-described construction, when the screw rod is rotated relative to the piston rod in setting the injection amount, the screw rod moves rearward axially relative to the body section of the injection apparatus.

Preferably, the stopper member is made of a frictional/elastic material such as a rubber. That is, it is made of a material which is superior in frictional property. The front step surface of the piston rod is an inclined surface which extends from the bottom surface outwardly in the radial direction and towards a front side of the piston rod, and a wedge-shaped space is formed between the inclined surface and the inner peripheral surface of the guide sleeve.

In the above-described construction, when the piston rod is returned from the pushing-in position to the initial position by the spring means, and the stopper member reaches the wedge-shaped space between the inclined surface of the groove and the inner peripheral surface of the guide sleeve, the stopper member fits in the wedge-shaped space as the stopper member is elastically deformed. As a result, there is an increase in the frictional force between the stopper member and the inner peripheral surface of the guide sleeve and between the stopper member and the inclined surface of the piston rod.

Accordingly, with the above-described construction, the piston rod is reliably fixed to the guide sleeve at the initial position.

In the above-described construction, if the pushing-in amount of the screw rod is smaller than the stroke of the stopper member which moves between the front step surface of the piston rod and the rear step surface thereof, the stopper member is not pressed by the rear step surface of the piston rod when the screw rod is pushed in. As a result, the stopper member remains stationary relative to the inner peripheral surface of the guide sleeve. Thus, when the pressed piston rod is pulled backward by the spring means, the screw rod returns to the same position as before it was pushed in. Therefore, the position of the screw rod makes it impossible to determine whether an injection has been given to a patient or not. It is preferable to provide the following construction in order to eliminate such inconvenience.

That is, preferably, the stroke of the stopper member moving between the front step surface of the piston rod and the rear step surface thereof is smaller than the amount of the screw rod which is fed relative to the piston rod by rotating the screw rod to set a dosage amount for injection.

In the above-described construction, when the piston rod is pressed, the stopper member is reliably brought into contact with the rear step surface of the piston rod so that the stopper member is pushed in and moved. The movement amount thereof is greater than the stroke of the stopper member which moves between the front step surface of the piston rod and the rear step surface thereof. Thus, when the piston rod is moved backward by the spring means, the stopper member never fails to contact the front step surface of the piston rod. That is, after an injection is carried out, the piston rod is returned from the pushing-in position to the initial position in correspondence to the stroke of the stopper member which moves between the front step surface of the piston rod and the rear step surface thereof. Thus, the position of the rear end of the screw rod relative to the injection apparatus is unchanged.

Therefore, the screw rod is not returned to the position at which it is fed rearward in order to set an injection amount, but the screw rod is returned to a predetermined position relative to the body section of the injection apparatus. Thus, it is easy to determine whether injection of the set injection amount has been given to the patient or not.

Preferably, the concave is formed as a circumferential concave, and the stopper member is a ring-shaped one provided on the circumferential concave.

According to the above-described construction, the number of parts to be used is small and the configuration is simple; thus, it is the most preferable.

BEST MODE FOR CARRYING OUT THE INVENTION

An injection apparatus according to each embodiment of the present invention shown in FIGS. 2 through 21 is described below in detail.

A first embodiment is described below with reference to FIGS. 2 through 14.

Figure 1:
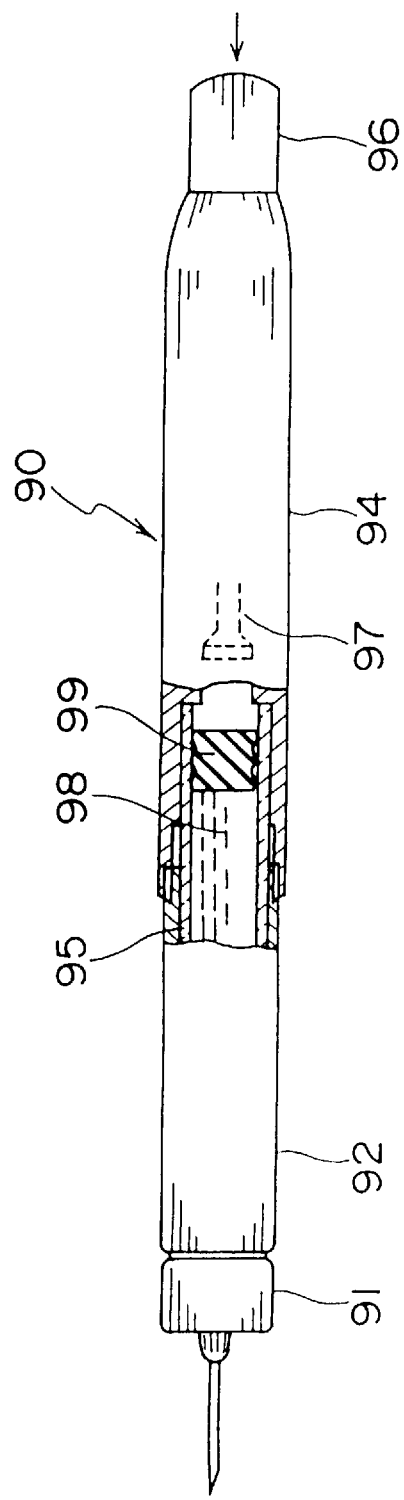
FIG. 1 is a front view partly in section showing a conventional injection apparatus.
Figure 2A:
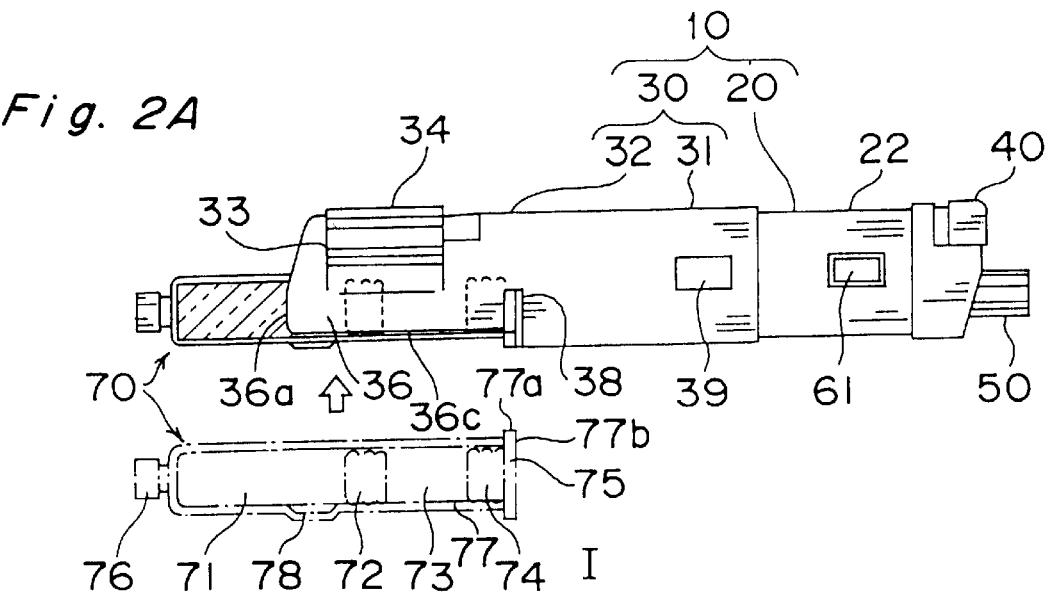
FIGS. 2A–2D are front views showing an injection apparatus according to a first embodiment of the present invention, FIGS. 2A through 2D correspond to states I through IV, respectively.

As shown in FIG. 2A, an injection apparatus 10 comprises a body section 20 and a movable section 30. The body section 20 has a release button 40 and an operation knob 50 at the rear end thereof and an indicator 61 at one side thereof. The body section 20 fits in the rear casing 31 of the movable section 30. A front casing 32 of the movable section 30 has an operation knob 34 positioned at an upper cut-out 33 thereof and an ampule holding part 36 at a lower portion thereof.

An ampule 70 particularly preferable for the injection apparatus 10 is a two-component ampule as shown by chain lines in FIG. 2A and has a flange 75 at an end thereof opposite to an end thereof on which a needle-mounting part 76 is mounted. The ampule 70 has two pistons 72 and 74 inside a syringe 77 thereof. One component of the two-component agent (base) is contained in a first chamber 71 and the other component thereof is contained in a second chamber 73 partitioned from the first chamber 71. For example, a dry powder agent (base) prepared by freeze drying is contained in the first chamber 71, while disolving agent (base) separate from the powder agent (base) is contained in the second chamber 73. Both components are mixed with each other at time of injection.

As shown by an arrow in FIG. 2A, the ampule 70 is inserted into the ampule holding part 36 from below the front casing 32 of the movable section 30, and the operation knob 34 is rotated to move the movable section 30 rearward together with the ampule 70. Then, a needle unit 80 is mounted on the needle-mounting part 76 of the ampule 70 to set the ampule 70 on the injection apparatus 10, as shown in FIG. 2D. After the ampule 70 is set on the injection apparatus 10, the operation knob 50 is rotated to set an injection amount, and then, pressed axially to carry out an injection.

The construction of the injection apparatus 10 will be described further in detail with reference to FIGS. 2A, 4, and 11.

Figure 4:
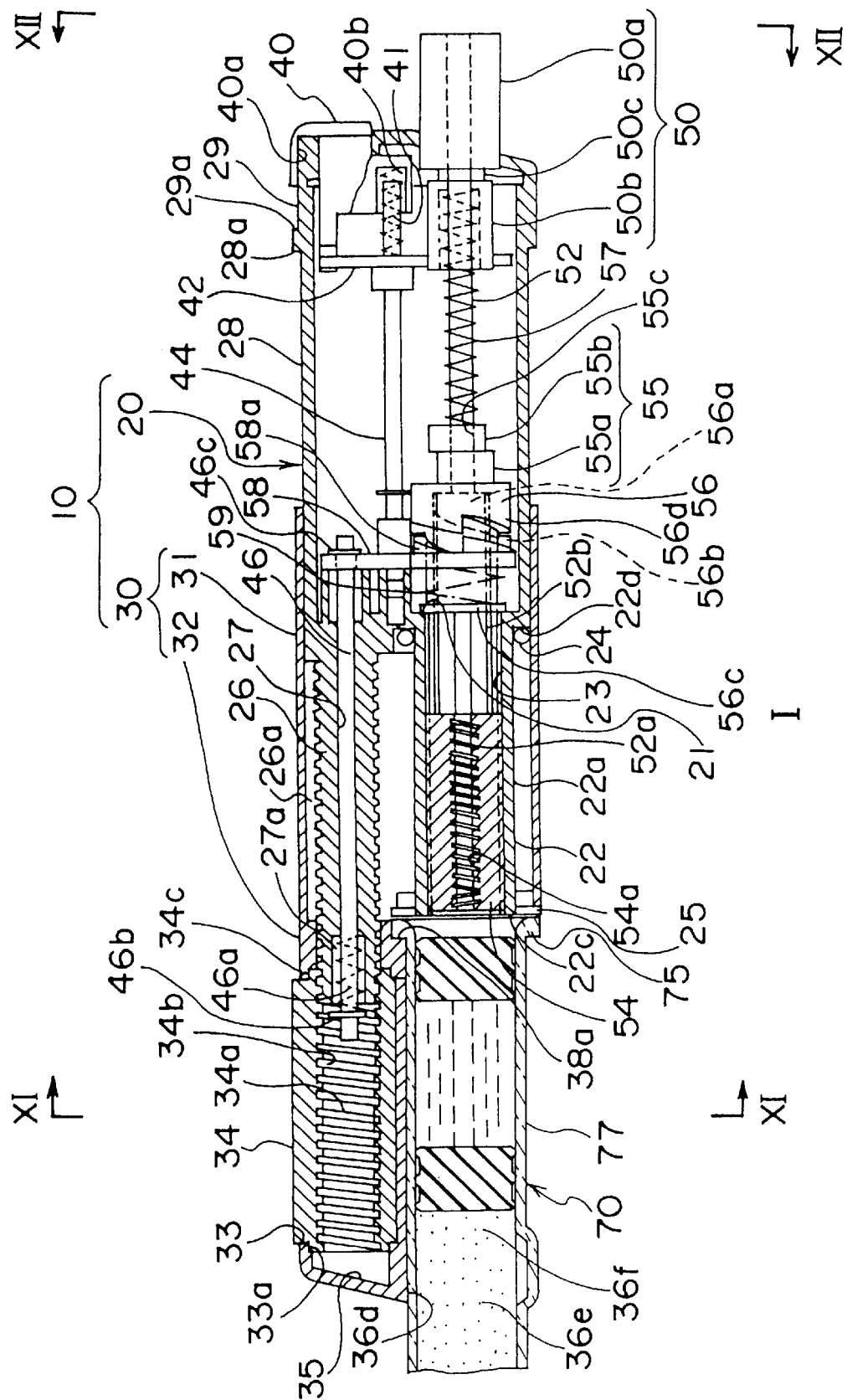
FIG. 4 is an enlarged sectional view showing the injection apparatus in the state I shown in FIG. 2A.

FIG. 4 is a sectional view corresponding to an initial state shown in FIG. 2A. In the injection apparatus 10, a cylindrical guiding wall 28 constituting the casing of the body section 20 slidably fits in the rear casing 31 of the movable section 30. In the body section 20, a guide sleeve 22 projects forward concentrically with the axis of the ampule 70 (hereinafter referred to as merely "axis") when the ampule 70 is set on the injection apparatus 10, and a guide screw shaft 26 projects forward in parallel with the axis.

The guide sleeve 22 has a peripheral surface 22a, the outer diameter of which is generally equal to an inner diameter of the syringe 77 of the ampule 70. As shown in FIG. 11, showing the injection apparatus in a direction perpendicular to the axis, a peripheral cut-out 22b is formed on a part of the peripheral surface 22a. An O-ring 24 is provided on a base part 22d of the guide sleeve 22. A spacer 25 which freely engages the peripheral surface 22a of the guide sleeve 22 is provided ahead of the O-ring 24. The outer diameter of the spacer 25 is generally equal to that of the flange 75 of the ampule 70.

A through-hole 23 is formed in the guide sleeve 22. A piston rod 54 engages the through-hole 23 nonrotatably and movably in its axial direction. That is, as shown in FIG. 11, the through-hole 23 of the guide sleeve 22 is generally circular in section, and projections 23a project inward from the guide sleeve in four directions, each adjacent one of which forms a 90° angle. On the other hand, the sectional configuration of the piston rod 54 corresponds to that of the through-hole 23. Thus, the piston rod 54 is movable axially through the through-hole 23 without rotating therein. In an initial state, the piston rod 54 is retracted inside the through-hole 23 of the guide sleeve 22, and a front end 22c of the guide sleeve 22 and that of the piston rod 54 are generally in the same plane.

The piston rod 54 has a hole in its center, and a female screw 54a is formed on the hole. A screw rod 52 having a male screw 52a, which engages the female screw 54a, formed on a front part thereof and having the operation knob 50 fixed to the rear end thereof is connected with the piston rod 54 by means of the screws.

The screw rod 52 penetrates through a through-hole 56a of a ratchet 56 and a through-hole 55c of an encoder cam 55. The ratchet 56 positioned forward and the encoder cam 55 positioned rearward are fixed to each other and they rotate without moving axially.

The screw rod 52 has a spline shaft portion 52b projecting outward at an intermediate part thereof. A spline part 56b is formed at a front side of the through-hole 56a of the ratchet 56. The spline shaft portion 52b of the screw rod 52 engages the spline part 56b of the ratchet 56. Thus the screw rod 52, the ratchet 56, and the encoder cam 55 always rotate together.

The screw rod 52 has a return spring 57 between the encoder cam 55 and the operation knob 50. The return force of the return spring 57 always urges the screw rod 52 backward.

A flange 56c is formed at a front end of the ratchet 56. The return force of the return spring 57 causes the flange 56c to be always in contact with a ratchet contact part 21 of the body section 20.

The ratchet 56 has a ratchet part 56d, facing forward, formed in back of the flange 56c. A rotation regulation plate 58 positioned between the ratchet part 56d and the flange 56c, and having a through-hole through which the ratchet 56 penetrates, is mounted axially movable to the body section 20. A ratchet 58a facing the ratchet part 56d of the ratchet 56 is formed on a rear side of the rotation regulation plate 58. A return spring 59 is provided between the front side of the rotation regulation plate 58 and the ratchet contact part 21 of the body section 20. The return force of the return spring 59 urges the rotation regulation plate 58 backward, thus always allowing engagement between the ratchet 58a of the rotation regulation plate 58 and the ratchet portion 56d of the ratchet 56.

A guide screw shaft 26 of the body section 20 will be described below. The guide screw shaft 26 projects forward in parallel with the axis. A male screw 26a is formed on the periphery of the guide screw shaft 26, and a through-hole 27 is formed in the center thereof.

The male screw 26a engages a female screw 34a formed in a center hole of the operation knob 34 of the movable section 30.

A rotation regulation release pin 46 penetrates through the through-hole 27. A spring accommodating part 27a is formed at the front side of the through-hole 27. A spring flange 46b is fixed to a front end of the rotation regulation release pin 46. A return spring 46a is provided between the spring flange 46b and the spring accommodating part 27a. The return force of the return spring 46a urges the rotation regulation release pin 46 forward.

On the other hand, the rear end of the rotation regulation release pin 46 penetrates through the rotation regulation plate 58, and a release flange 46c is fixed to the rotation regulation release pin 46 behind the rotation regulation plate 58. When the rotation regulation release pin 46 is moved forward, the rotation regulation plate 58 is moved forward by the release flange 46c.

The movable section 30 will be described below. As shown in FIGS. 2A, 4, and 11, the ampule holding portion 36 is formed at a lower part of the front casing 32 of the movable section 30. That is, the ampule holding part 36 comprises a pair of ampule securing elastic wings 36a formed on both sides of a lower part of the front casing 32. As shown in FIG. 11, the pair of ampule securing elastic wings 36a is generally C-shaped in its sectional view taken perpendicular to the axis. The inner peripheral surface of the pair of ampule securing elastic wings 36a forms an ampule insertion space 36f into which the ampule 70 is inserted. The diameter of the inner peripheral surface of the pair of ampule securing elastic wings 36a is generally equal to the outer diameter of the syringe 77 of the ampule 70. A side edge 36b at a lower inner side of each ampule securing elastic wing 36a forms a lower opening 36c. Further, the front end 36d of the pair of ampule securing elastic wings 36a forms a front opening 36e. The distance between both side edges 36b of the pair of ampule securing elastic wings 36a is shorter than the outer diameter of the syringe 77 of the ampule 70 by a predetermined amount.

A center of the lower part of the front casing 32 is cut out to form a flange insertion part 38 into which the flange 75 of the ampule 70 is inserted. The spacer 25 is positioned at the flange insertion part 38, and the rear side of the spacer 25 fits in the front casing 32 of the movable section 30.

The operation knob 34 which is unmovable axially and rotatable is provided on the upper cut-out 33 of the front casing 32. A through-hole 34a is formed in the center of the operation knob 34, and a screw 34b is formed on the inner peripheral surface of the operation knob 34. The female screw 34b engages the male screw 26a formed on the periphery of the guide screw shaft 26 of the body section 20. The operation knob 34 has a bearing part 34c formed at each end thereof and is supported by a bearing part 33a of the front casing 32.

The rear casing 31 of the movable section 30 is cut out at a predetermined position thereof to form a display window 39 to which a transparent plate is fixed. An indicator 61 of the body section 20 is seen through the display window 39 when the ampule 70 is set in the injection apparatus 10.

Description of the method of operating the injection apparatus 10 and the detailed construction thereof, will be made below.

In the initial state shown in FIGS. 2A and 4, the ampule 70 is inserted from below into the ampule holding part 36 of the movable section 30 placed at the ampule insertion position.

At this time, the movable section 30 is forwarded from the body section 20 to its maximum, and the piston rod 54 is retracted inside the guide sleeve 22 of the body section 20, as described above. Because the guide sleeve 22 and the piston rod 54 are not projected into the ampule insertion space 36f at this time, the ampule 70 can be inserted into the ampule holding part 36 without interference. On the other hand, in an incomplete initial state, the guide sleeve 22 and/or the piston rod 54 project into the ampule insertion space 36f, so that the ampule 70 cannot be inserted into the ampule holding part 36. This is because they interfere with the ampule 70. That is, unless the injection apparatus 10 is in the complete initial state, the ampule 70 cannot be inserted into the ampule holding part 36.

In the initial state, the rotation regulation release pin 46 moves the rotation regulation plate 58 forward by means of the urging force of the return spring 46a against the urging force of the return spring 59 which urges the rotation regulation plate 58 backward. As a result, the ratchet 58a of the rotation regulation plate 58 and the ratchet part 56d of the ratchet 56 disengages from each other. Accordingly, the screw rod 52 can be rotated in both directions, and hence it is possible to move the piston rod 54 back.

Figure 11:
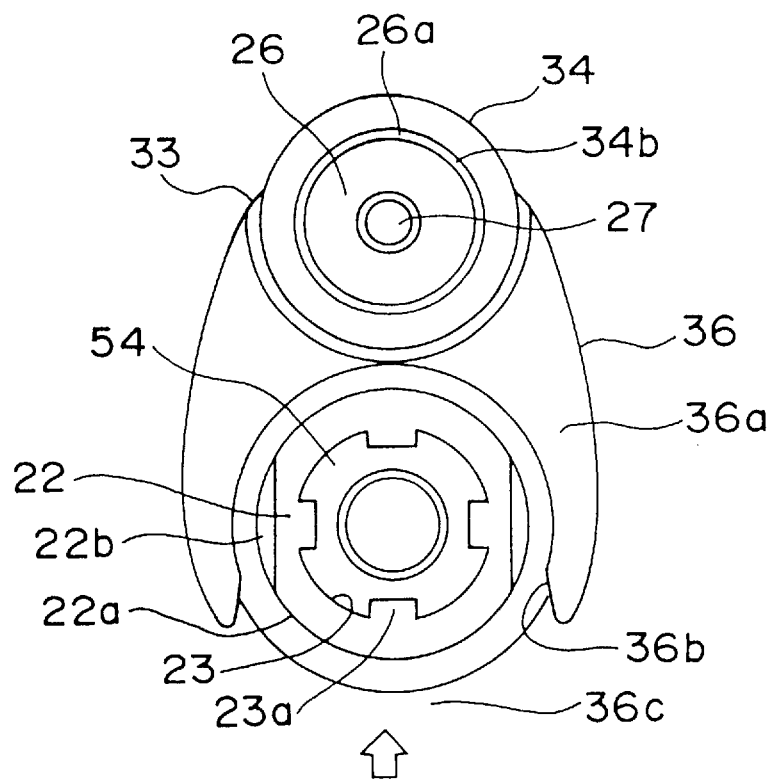
FIG. 11 is a sectional view taken along a line XI—XI of FIG. 4.
Figure 12:
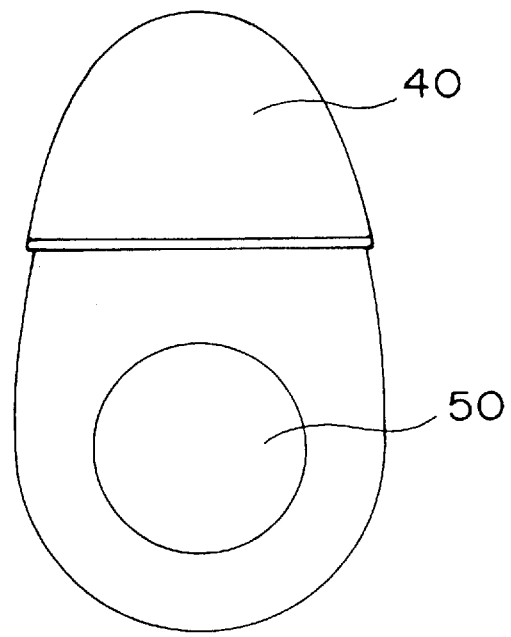
FIG. 12 is a sectional view taken along a line XII—XII of FIG. 4.
Figure 13:
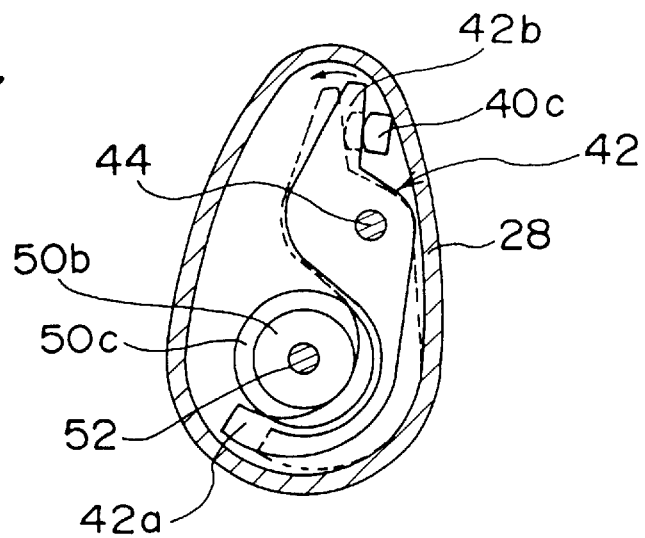
FIG. 13 is a sectional view taken along a line XIII—XIII of FIG. 6.

As shown in FIG. 11, in the ampule-inserting operation, the ampule 70 is pressed in the lower opening 36c of the pair of ampule securing elastic wings 36a. Then, the ampule securing elastic wings 36a are expanded outward, allowing insertion of the ampule 70 into the ampule insertion space 36f. After the ampule 70 is inserted thereinto, the ampule securing elastic wings 36a are returned to their original form, thus preventing the ampule 70 from moving in a direction perpendicular to the axis of the ampule 70. At the same time, the flange 75 of the ampule 70 is inserted into the flange insertion part 38, thus preventing the ampule 70 from moving in the axial direction as well. Accordingly, the ampule 70 is held temporarily in the axial direction and the direction perpendicular thereto.

Figure 2B:
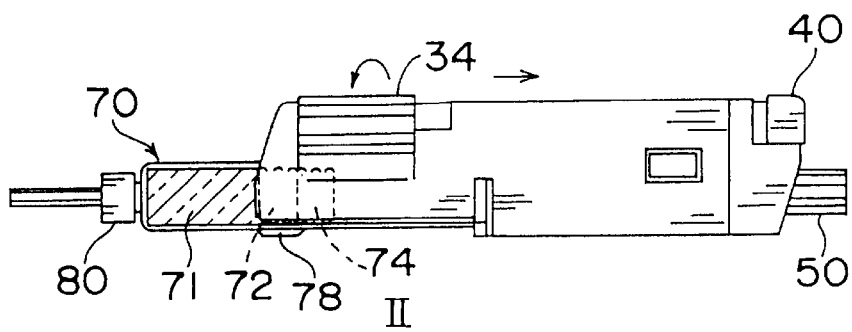
Figure 5:
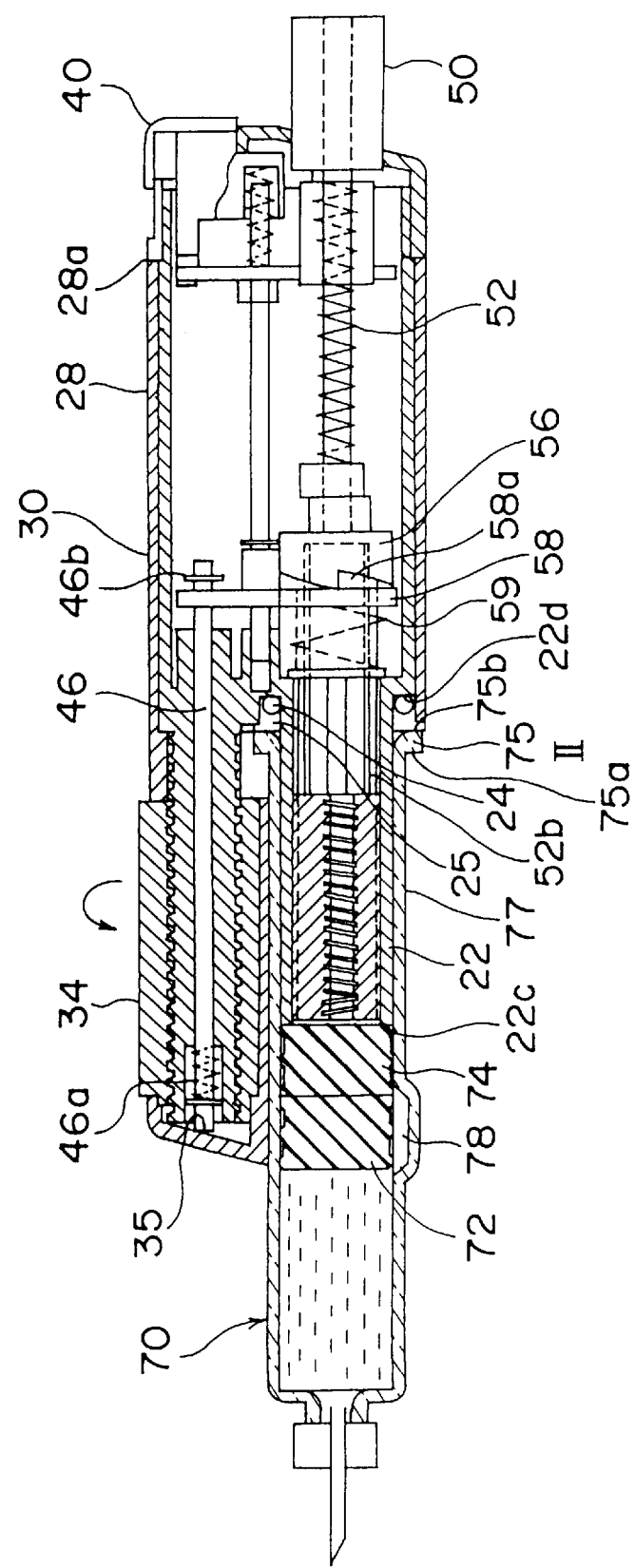
FIG. 5 is an enlarged sectional view showing the injection apparatus in the state II shown in FIG. 2B.

Then, as shown in FIGS. 2B and 5, the operation knob 34 is rotated in a predetermined direction to move the movable section 30 to a setting position at which the movement of the ampule 70 is completed.

That is, the female screw 34b of the operation knob 34 of the movable section 30 engages the male screw 26a of the guide screw shaft 26 of the body section 20. Thus, due to the rotation of the operation knob 34, the operation knob 34 moves along the guide screw shaft 26. As a result, the entire movable section 30 moves relative to the body section 20. Thus, the entire movable section 30 is moved toward the body section 20 by rotating the operation knob 34 in a predetermined direction.

Because the flange 75 of the ampule 70 has fitted in the flange insertion part 38 of the movable section 30, the ampule 70, held by the ampule holding part 36 of the movable section 30, moves toward the body section 20 together with the movable section 30. At this time, the guide sleeve 22 of the body section 20 is inserted into the syringe 77 of the ampule 70. The guide sleeve 22 can be inserted into the syringe 77 smoothly, with the peripheral surface 22a of the guide sleeve 22 in sliding contact with the inner peripheral surface of the syringe 77 of the ampule 70, because the peripheral cut-out 22b formed on the guide sleeve 22 reduces the frictional force between the peripheral surface 22a and the inner peripheral surface of the syringe 77.

The front end 22c of the guide sleeve 22 contacts the rear end surface of the second piston 74 of the ampule 70, thus pushing in the second piston 74. At the same time, the first piston 72 moves, with the medicine contained in the second chamber 73, allowing a predetermined interval to be kept between the first piston 72 and the second piston 74. When the first piston 72 reaches a bypass part 78 at which a portion of the inner peripheral surface of the syringe 77 projects outward, the first chamber 71 and the second chamber 73 communicate with each other through the bypass part 78. As a result, the medicine in the second chamber 73 moves from the rear side of the first piston 72 to the first chamber 71 through the bypass part 78, with the medicine in the second chamber 73 being pressed by the second piston 74. At this time, the first piston 72 does not move, but the second piston 74 moves until it contacts the first piston 72. In this manner, the medicine in the first chamber 71 and that in the second chamber 73 are mixed with each other. Depending on the kind of medicine, such mixture should be carried out very carefully and slowly. In such a case, the operation knob 34, the female screw 34b of the operation knob 34, and the male screw 26a of the guide screw shaft 26 may be appropriately selected in construction so that the medicines are mixed together slowly even if it is operated normally without taking much care.

When the guide sleeve 22 is inserted into the syringe 77 of the ampule 70, the ampule 70 is incapable of moving in a direction perpendicular to the axial direction thereof.

As the movable section 30 moves, a rear end surface 75b of the flange 75 of the ampule 70 pushes the spacer 25 installed around the guide sleeve 22. At the set position at which the movement of the movable section 30 is completed, the spacer 25 presses the O-ring 24 positioned at the base portion 22d of the guide sleeve 22. The flange 75 of the ampule 70 is urged forward through the spacer 25 by the elastic force of the O-ring 24, while a front end surface 75a of the flange 75 contacts a front end surface 38a of the flange insertion part 38 of the movable section 30. Accordingly, the ampule 70 is held free from backlash in the axial direction thereof.

Then, the needle unit 80 is installed on the needle-mounting part 76 of the ampule 70, and then air inside the syringe 77 of the ampule 70 is released.

Figure 2C:
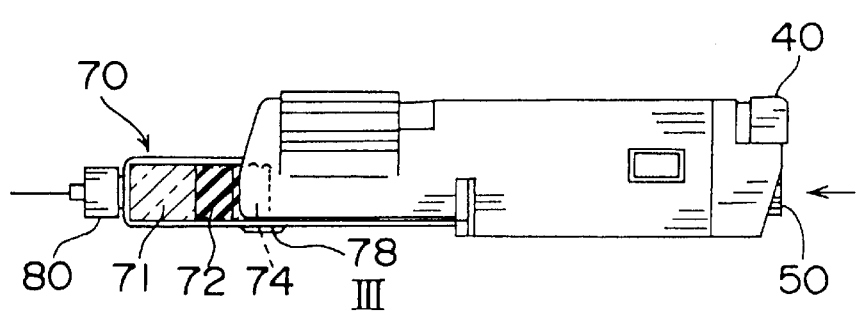
Figure 2D:
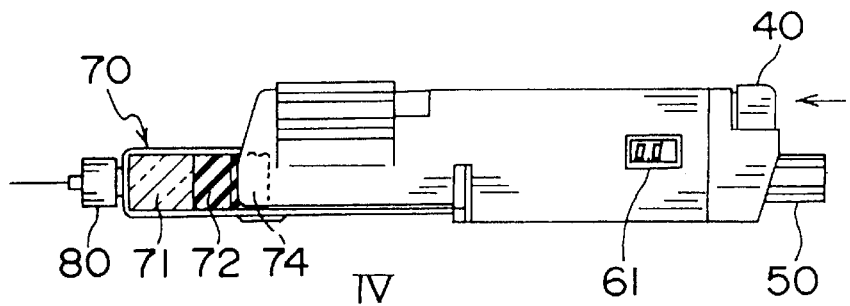
Figure 6:
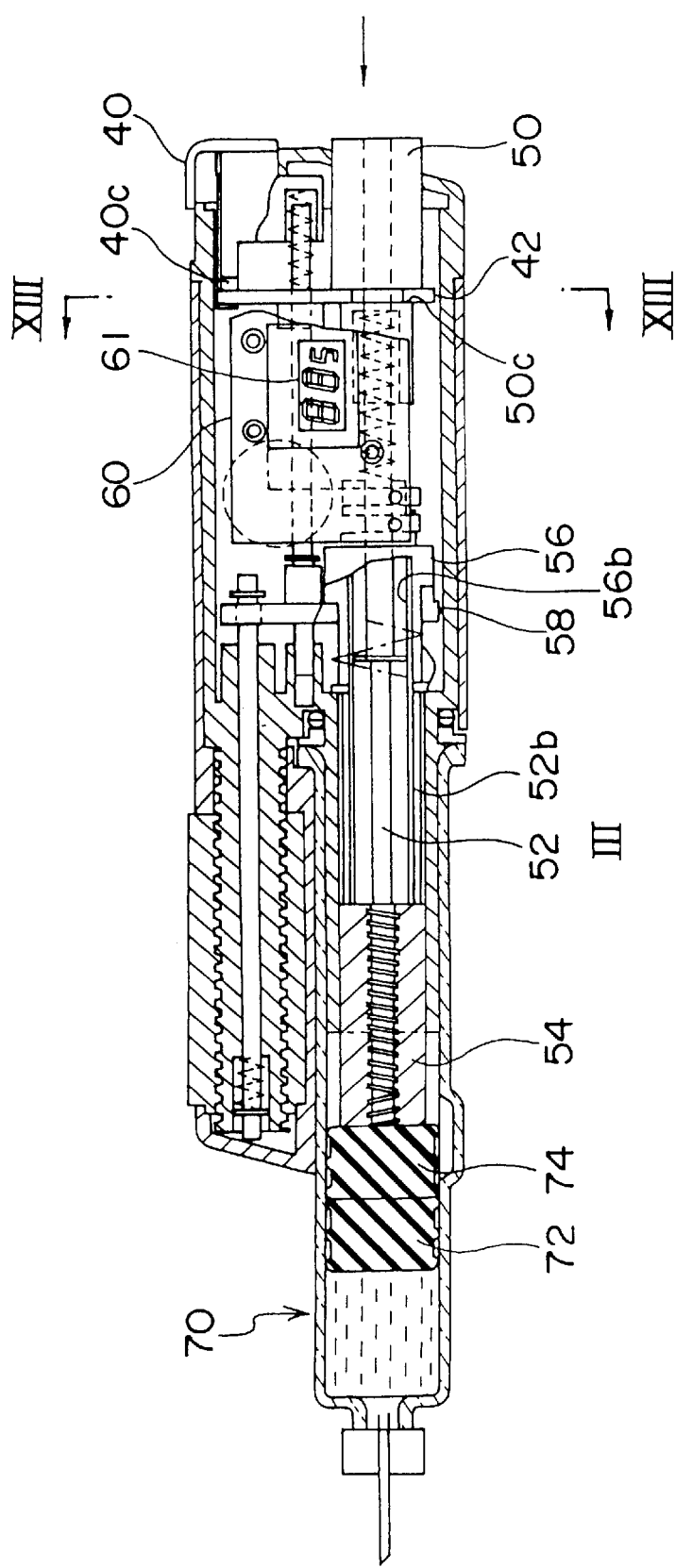
FIG. 6 is an enlarged sectional view showing the injection apparatus in the state III shown in FIG. 2C.

As shown in FIGS. 2C and 6, in order to release the air completely from the syringe 77, the piston rod 54 is moved forward to press the pistons 72 and 74 forward by pressing the operation knob 50 forward. At this time, the screw rod 52 moves together with the piston rod 54 from an initial position to a pressing position. That is, the spline shaft part 52b of the screw rod 52 moves axially forward from the initial position while the spline shaft part 52b keeps engaging the spline part 56b of the ratchet 56. Then, a stopper strip 42a of a stopper plate 42 fits in a stopper groove 50c of the operation knob 50, thus providing the pressing position.

Figure 7:
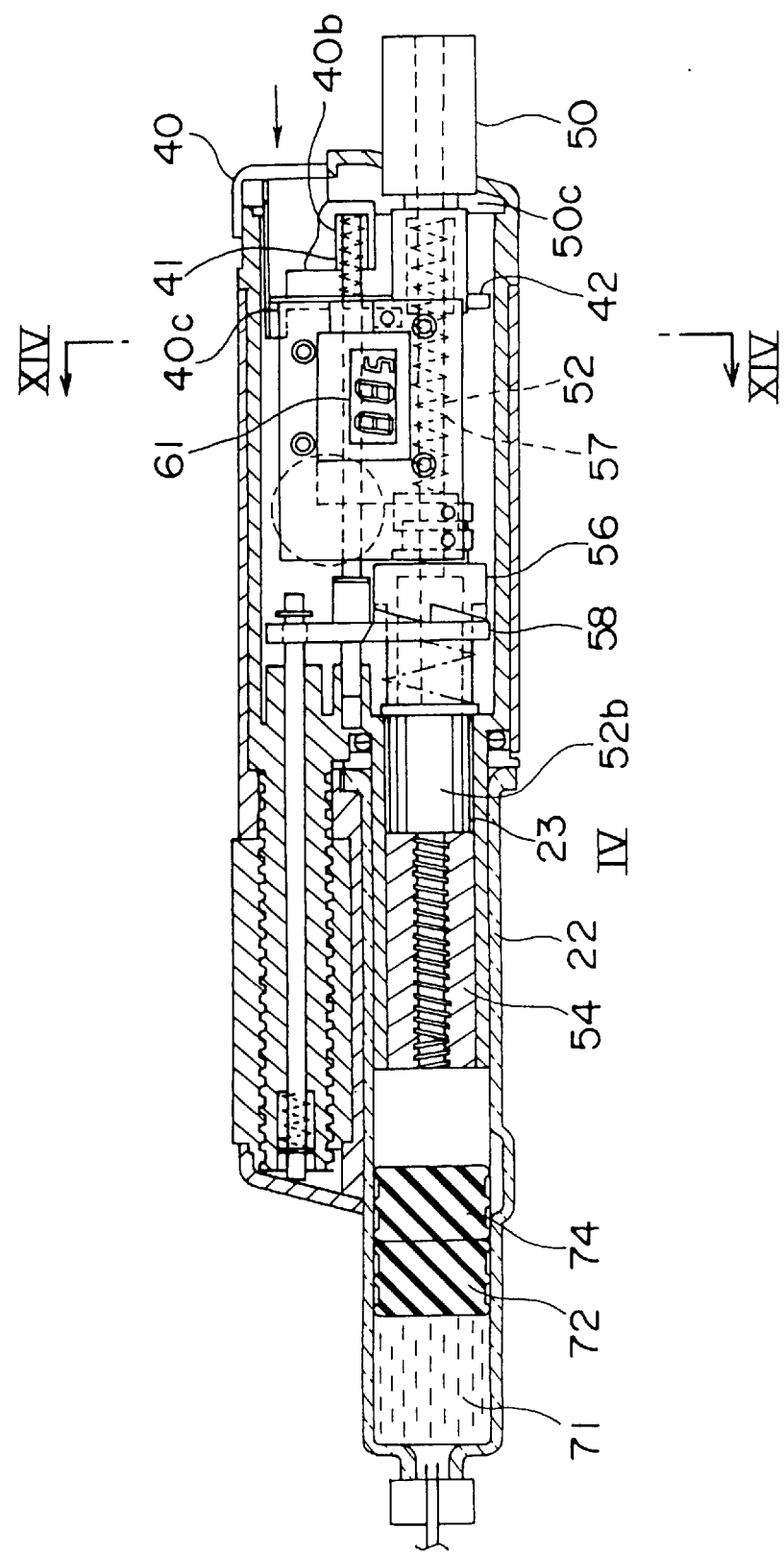
FIG. 7 is an enlarged sectional view showing the injection apparatus in the state IV shown in FIG. 2D.

Then, the release button 40 is pressed to return the screw rod 52 and the piston rod 54 to the initial position, as shown in FIGS. 2D and 7. At this time, as shown by a dotted line of FIG. 13, a stopper release part 40c of the release button 40 moves a reset strip 42b of the stopper plate 42 to the left side in FIG. 13, thus rotating the stopper plate 42 on a stopper-supporting pin 44. As a result, the stopper strip 42a is unlocked from the stopper groove 50c of the operation knob 50. Then, the screw rod 52 and the piston rod 54 are returned to the initial position by the return force of the return spring 57. The return thereof to the initial position is detected by a stopper position detector (not shown).

In this state, the setting of the ampule 70 is completed. The indicator 61 displays an initial value 0.0 upon receipt of signals outputted from the stopper position detector.

Figure 3A:
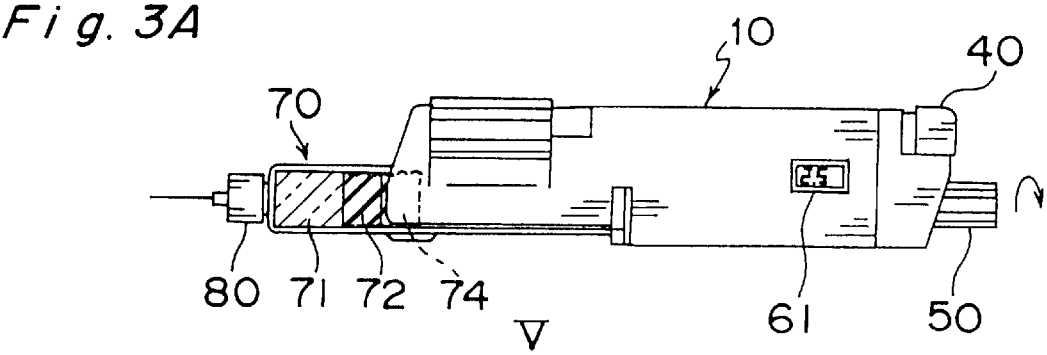
FIGS. 3A–3D are front views showing the injection apparatus according to the first embodiment of the present invention, FIGS. 3A through 3D correspond to states V through VIII, respectively.
Figure 8:
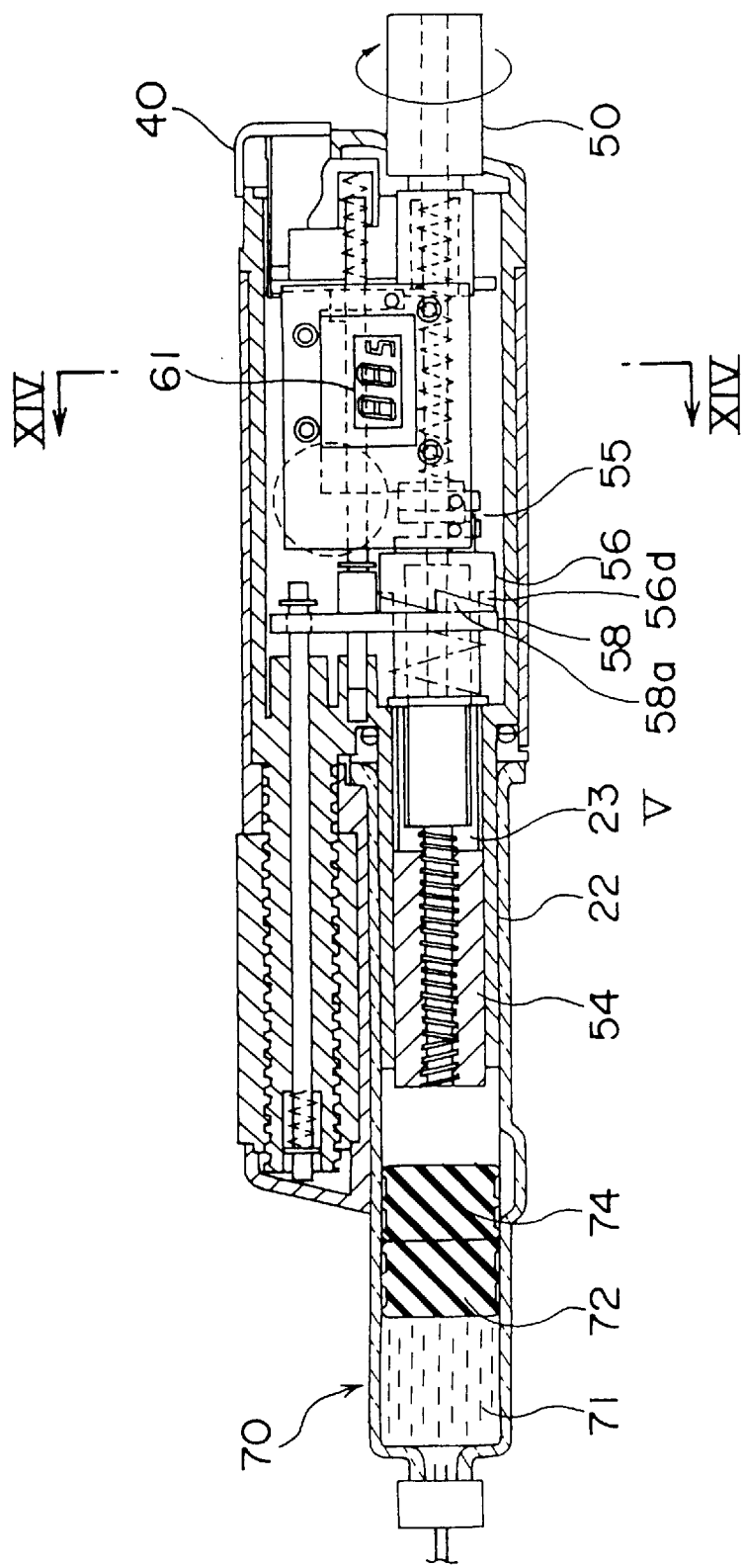
FIG. 8 is an enlarged sectional view showing the injection apparatus in the state V shown in FIG. 3A.

Then, in order to set an injection amount, the operation knob 50 is rotated in a predetermined direction, as shown in FIGS. 3A and 8. By the operation, the piston rod 54 is moved forward relative to the screw rod 52. The amount of the forward movement of the piston rod 54 corresponds to the injection amount. When the screw rod 52 is rotated in the predetermined direction, the contact inclined surface of the ratchet part 56d of the ratchet 56 presses the ratchet 58a of the rotation regulation plate 58 forward against the return force of the return spring 59. Thus, the screw rod 52 is rotatable. When the screw rod 52 is rotated in the opposite direction, the surface of the ratchet part 56d in the axial direction and that of the ratchet 58a in the axial direction engage each other, thus preventing rotation of the screw rod 52. Accordingly, the operation knob 50 is rotatable only in the direction in which the injection amount can be set by moving the piston rod 54 forward.

Figure 14:
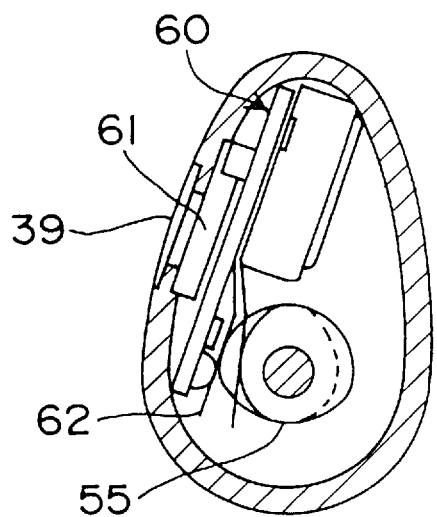
FIG. 14 is a sectional view taken along a line XIV—XIV of FIG. 7.

As shown in FIG. 14 which is a sectional view of the injection apparatus 10, the amount of rotation of the screw rod 52 made by rotating the operation knob 50 is detected by a detection switch 62, the contact point of which is opened and closed depending on the position of the encoder cam 55. Upon receipt of signals outputted from the detection switch 62, the indicator 61 displays an injection amount corresponding to the signals.

Figure 3B:
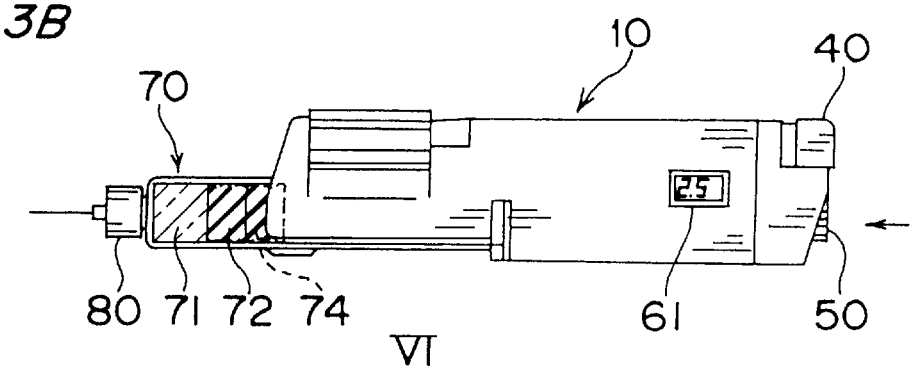
Figure 9:
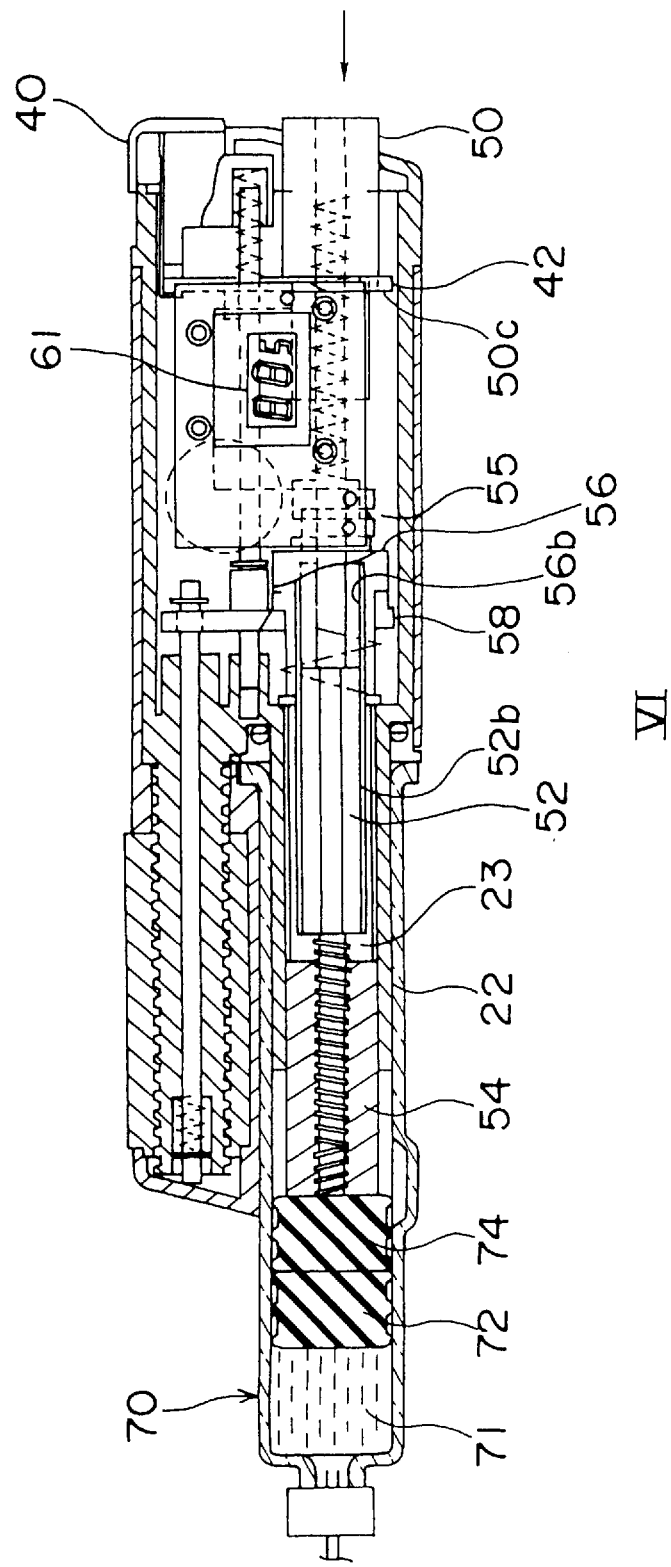
FIG. 9 is an enlarged sectional view showing the injection apparatus in the state VI shown in FIG. 3B.

As shown in FIGS. 3B and 9, after the injection amount is set, injection is carried out by pressing the operation knob 50 forward after a patient is pricked with the needle. Because the piston rod 54 has moved forward in correspondence to the amount of the rotation of the operation knob 50 made immediately before the operation knob 50 is pressed forward, the pistons 72 and 74 are pushed forward in correspondence to the amount of the forward movement of the piston rod 54.

Figure 3C:
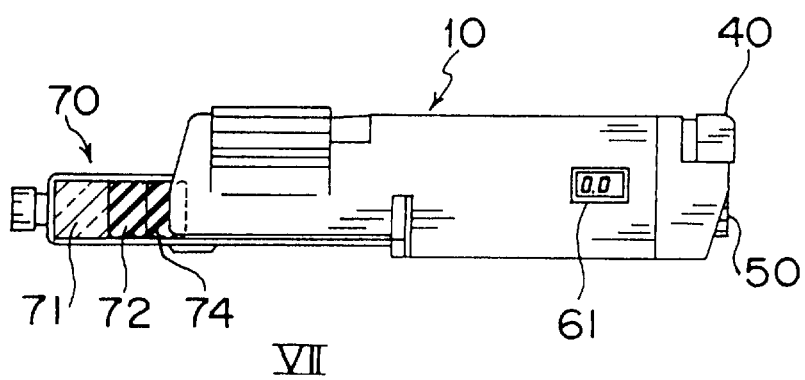

After one dosage of injection is completed, the needle unit 80 is removed from the ampule 70 as shown in FIG. 3C and it can be stored.

When injections are repeatedly performed, the release button 40 is pushed forward to return the screw rod 52 and the piston rod 54 to the initial position, as described above. At this time, the indicator 61 displays the initial value 0.0 upon receipt of signals outputted from the stopper position detector (not shown).

Figure 3D:
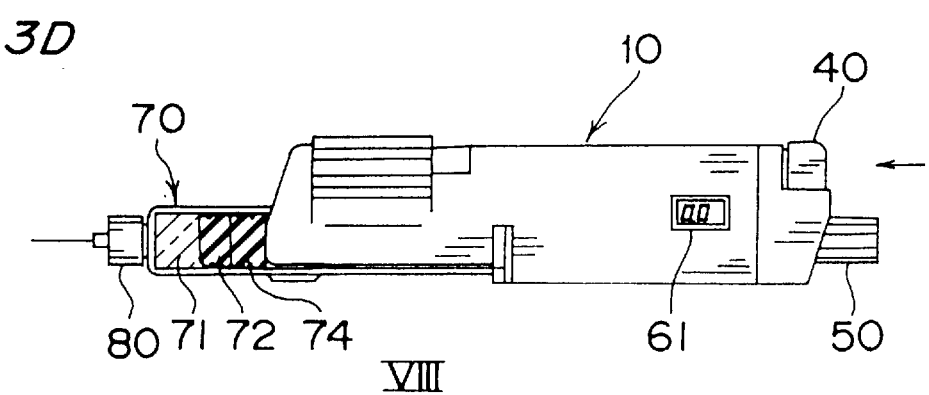
Figure 10:
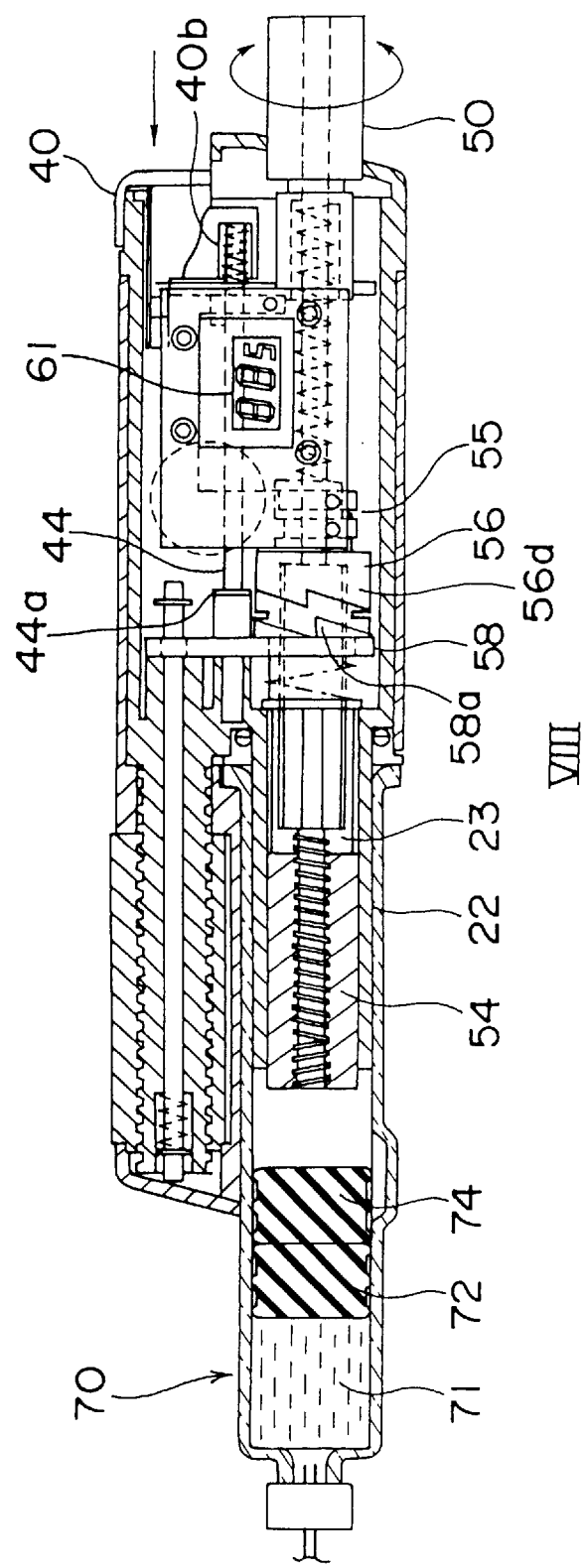
FIG. 10 is an enlarged sectional view showing the injection apparatus in the state VIII shown in FIG. 3D.

When the ampule 70 is removed from the injection apparatus 10, the screw rod 52 is returned to the initial position, and the operation knob 50 is rotated reversely. Because the ratchet 56 and the rotation regulation plate 58 prevent the reverse rotation of the operation knob 50, the release button 40 is pressed deep to rotate the operation knob 50 reversely, as shown in FIGS. 3D and 10. That is, a rear end of the stopper-supporting pin 44 is pressed forward by the bottom surface of a spring-accommodating part 40b of the release button 40. As a result, a release flange 44a of the stopper-supporting pin 44 presses the rotation regulation plate 58 forward, thus disengaging the ratchet part 56d of the ratchet 56 and the ratchet 58a of the rotation regulation plate 58 from each other. Accordingly, the screw rod 52 can be rotated reversely.

By rotating the operation knob 50 reversely, the piston rod 54 is returned into the guide sleeve 22 completely so as to return the movable section 30 to the ampule insertion position in a procedure opposite to that described above. At this time, because the ampule 70 is temporarily held by the ampule securing elastic blades 36a and the flange insertion portion 38 in the axial direction and the direction perpendicular thereto, the ampule 70 can be prevented from falling out of the injection apparatus 10. The ampule 70 is pulled downward from the injection apparatus 10 in a direction perpendicular to the axial direction against the elastic force of the securing elastic blades 36a.

With the above-described construction of the injection apparatus 10, the ampule 70 can be easily installed thereon; in addition, the state of the injection liquid inside the ampule 70 can be easily seen.

The present invention is not limited to the above-described embodiment, but may be embodied in various other modes. For example, the driving means for moving the movable section relative to the body section may be constituted by a rack and a pinion.

In respect of the piston rod means of the first embodiment, when the operation knob 50 is rotated to set an injection amount, the piston rod 54 is fed forward and the screw rod 52 is stationary with respect to the body section 20. On the other hand, it is possible to feed the screw rod rearward by rotating the operation knob, with the piston rod being stationary.

Figure 15:
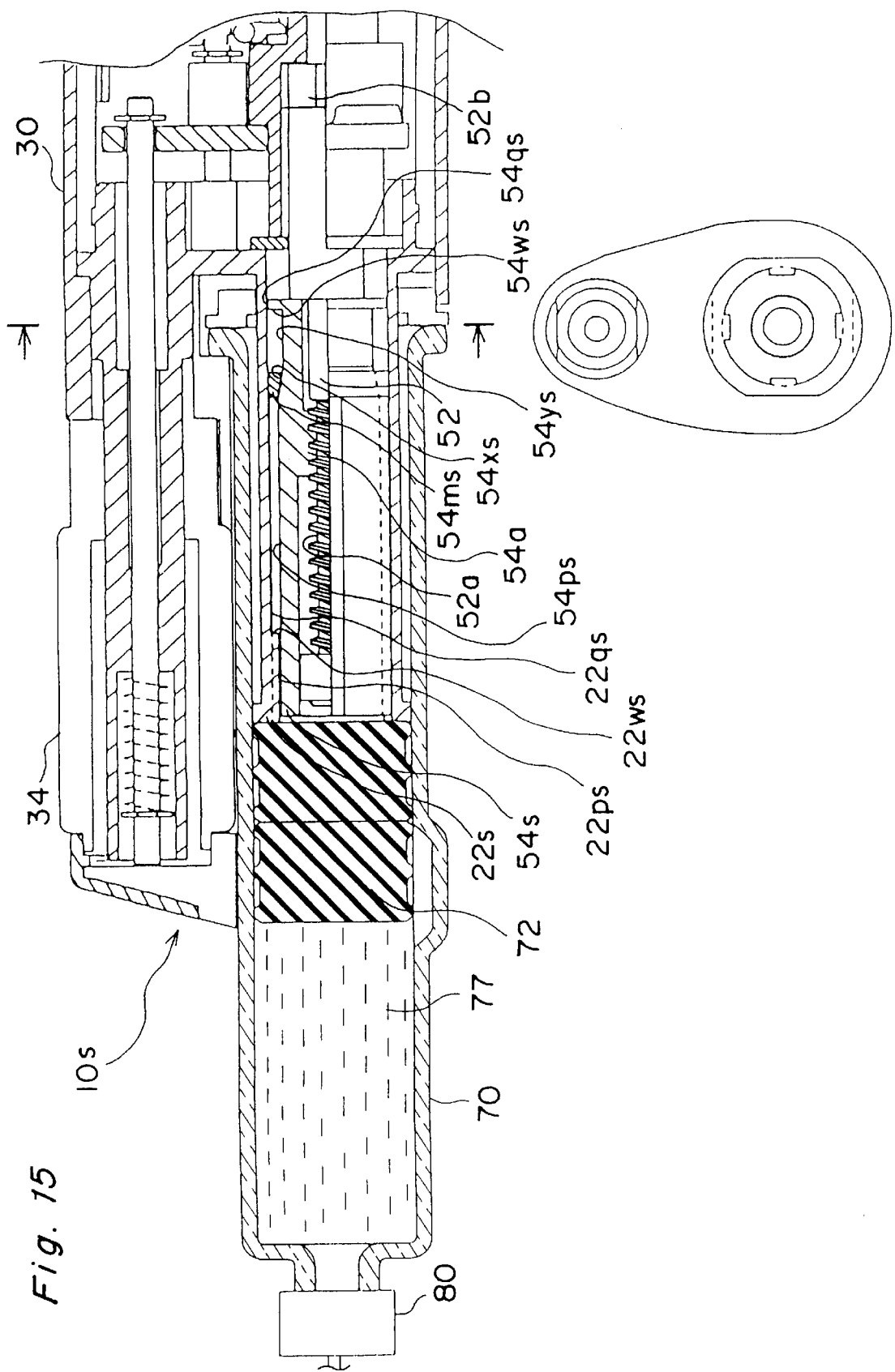
FIG. 15 is an enlarged sectional view showing an injection apparatus according to a second embodiment of the present invention, and the state of the injection apparatus corresponds to the state II shown in FIG. 2B.
Figure 16:
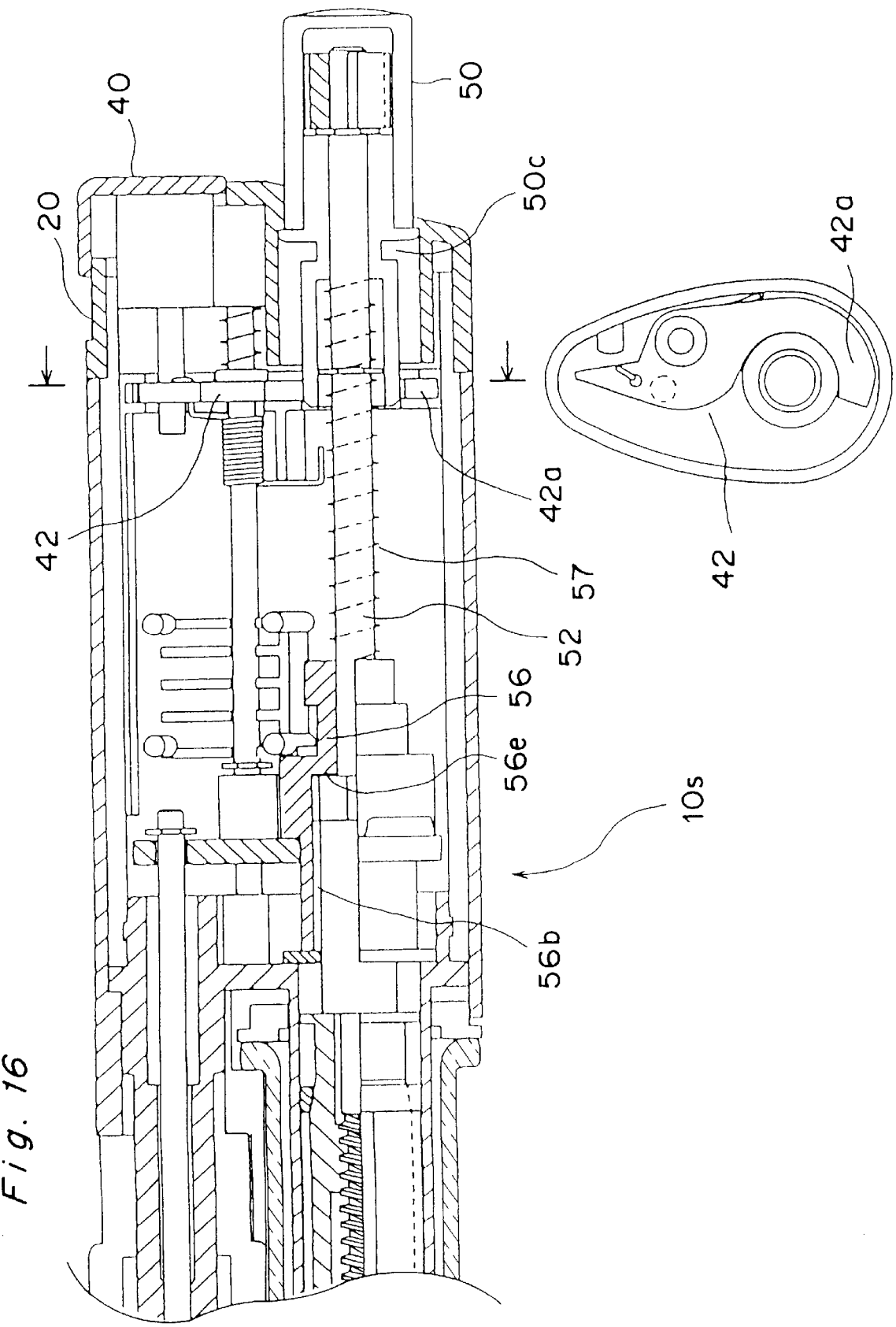
FIG. 16 is an enlarged sectional view showing the injection apparatus according to the second embodiment of the present invention, and the state of the injection apparatus corresponds to the state II shown in FIG. 2B.

An injection apparatus according to a second embodiment of the present invention will be described below in detail with reference to FIGS. 15 through 21. FIGS. 15 and 16 are enlarged sectional views showing an injection apparatus when an ampule is installed in the injection apparatus. FIGS. 17 through 21 are sectional views showing the injection apparatus at each operational step.

The injection apparatus of the second embodiment is constructed similarly to the first embodiment except the piston rod means. Description will be made below mainly on the points of the second embodiment which are different from the first embodiment. It is to be noted that in FIGS. 15 through 21, component parts of the second embodiment having the same constructions as those of the first embodiment are denoted by the same reference numerals, respectively, whereas component parts of the second embodiment having different constructions from those of the first embodiment are denoted by attaching a suffix "s" to reference numerals of the first embodiment to distinguish them from each other.

The construction of the piston rod means of an injection apparatus 10s of the second embodiment is substantially the same as that of the piston rod of the first embodiment. That is, as shown in FIGS. 15 and 16, similarly to the first embodiment, a piston rod 54s has a hole in its center, and a female screw 54a is formed on the hole and connected with a male screw 52a formed at a front end of the screw rod 52.

Unlike the first embodiment, the peripheral surface of the piston rod 54s is constructed stepwise. That is, a groove is circumferentially formed at a center of the peripheral surface of the piston rod 54s. The outer diameter of a front sliding part 54ps defining the peripheral surface of the front side of the piston rod 54s is smaller than that of a rear sliding part 54qs defining the peripheral surface of the rear side thereof. A stopper sliding part 54ys is formed at the rear side of the bottom surface of the groove, whereas a tapered part 54xs is formed at the front side of the bottom surface of the groove. The outer diameter of the stopper sliding part 54ys is smaller than that of the front sliding portion 54ps, and the tapered part 54xs is continuously, smoothly formed between the front sliding part 54ps and the stopper sliding part 54ys. A step 54ws is formed at the boundary between the stopper sliding part 54ys and the rear sliding part 54qs.

Unlike the first embodiment, the inner peripheral surface of a guide sleeve 22s is different from that of the first embodiment. That is, a front inner peripheral surface 22ps and a rear inner peripheral surface 22qs are formed stepwise. The inner diameter of the front inner peripheral surface 22ps is smaller than that of the rear inner peripheral surface 22qs, and a step 22ws is formed at the boundary between both inner peripheral surfaces 22ps and 22qs. The front inner peripheral surface 22ps of the guide sleeve 22s slides in contact with the front sliding portion 54ps of the piston rod 54s, and the rear inner peripheral surface 22qs of the guide sleeve 22s slides in contact with the rear sliding part 54qs of the piston rod 54s.

The inner peripheral surface of a stopper ring 54ms serving as a stopper member, not used in the first embodiment, slidably engages the stopper sliding part 54ys of the piston rod 54s and the tapered part 54xs thereof. The peripheral surface of the stopper ring 54ms slides in contact with the rear inner peripheral surface 22qs of the guide sleeve 22s and is axially movable between the step 22ws of the guide sleeve 22s and the step 54ws of the piston rod 54s.

The frictional force of the stopper ring 54ms, which slides in contact with both the guide sleeve 22s and the piston rod 54s, satisfies the following condition.

That is, the frictional force Fo between the peripheral surface of the stopper ring 54ms and the rear inner peripheral surface 22qs of the guide sleeve 22s is greater than the frictional force Fi between the inner peripheral surface of the stopper ring 54ms and the stopper sliding part 54ys of the piston rod 54s and between the inner peripheral surface of the stopper ring 54ms and the tapered part 54xs thereof. That is, $$Fi < Fo \tag{1}$$

The return force (P) of the return spring 57 for urging the screw rod 52 rearward axially is greater than the frictional force Fi between the inner peripheral surface of the stopper ring 54ms and the stopper sliding part 54ys of the piston rod 54s and between the inner peripheral surface of the stopper ring 54ms and the tapered part 54xs thereof, and the return force (p) is smaller than the frictional force Fo between the peripheral surface of the stopper ring 54ms and the rear inner peripheral surface 22qs of the guide sleeve 22s. That is, $$Fi < P < Fo \tag{2}$$

As will be described later, a pullback force (T) for forcibly pulling the screw rod 52 rearward is greater than the frictional force Fo between the peripheral surface of the stopper ring 54ms and the rear inner peripheral surface 22qs of the guide sleeve 22s. That is, $$Fo < T \tag{3}$$

From the equations (1) through (3), the following equation (4) is established:

$$Fi < P < Fo < T \tag{4}$$

The method of operating the injection apparatus 10s and the construction thereof will be described below in detail. The injection apparatus 10s is operated similarly to the first embodiment, but the operations of the piston rod 54s and the screw rod 52 are different from those of the first embodiment.

Figure 17:
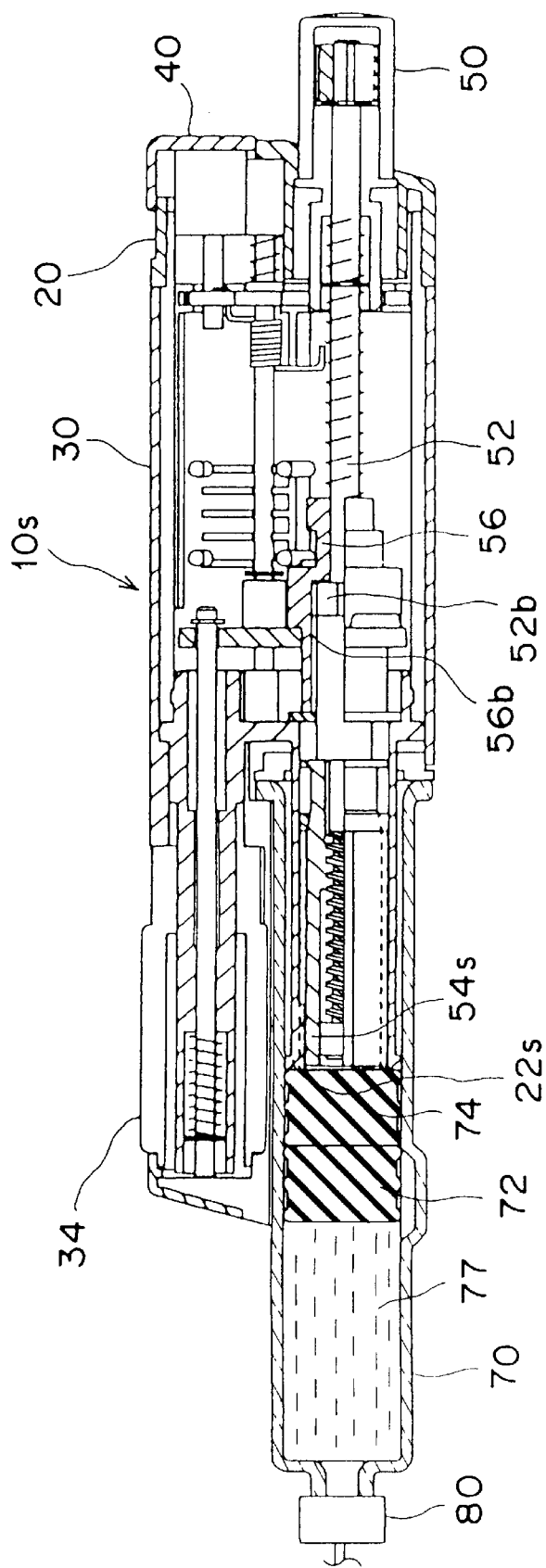
FIG. 17 is a sectional view showing the injection apparatus of FIGS. 15 and 16, and the state of the injection apparatus corresponds to the state II shown in FIG. 2B.

Similarly to the first embodiment, the ampule 70 is inserted into the injection apparatus 10s, the operation knob 34 is rotated to move the movable section 30 to the setting position, the needle unit 80 is installed on the needle-mounting portion, and then air inside the syringe 77 of the ampule 70 is released. The state at this time is shown in FIG. 17 corresponding to the state II of FIG. 2B, and in FIGS. 15 and 16 which are enlarged views of the injection apparatus 10s.

Figure 18:
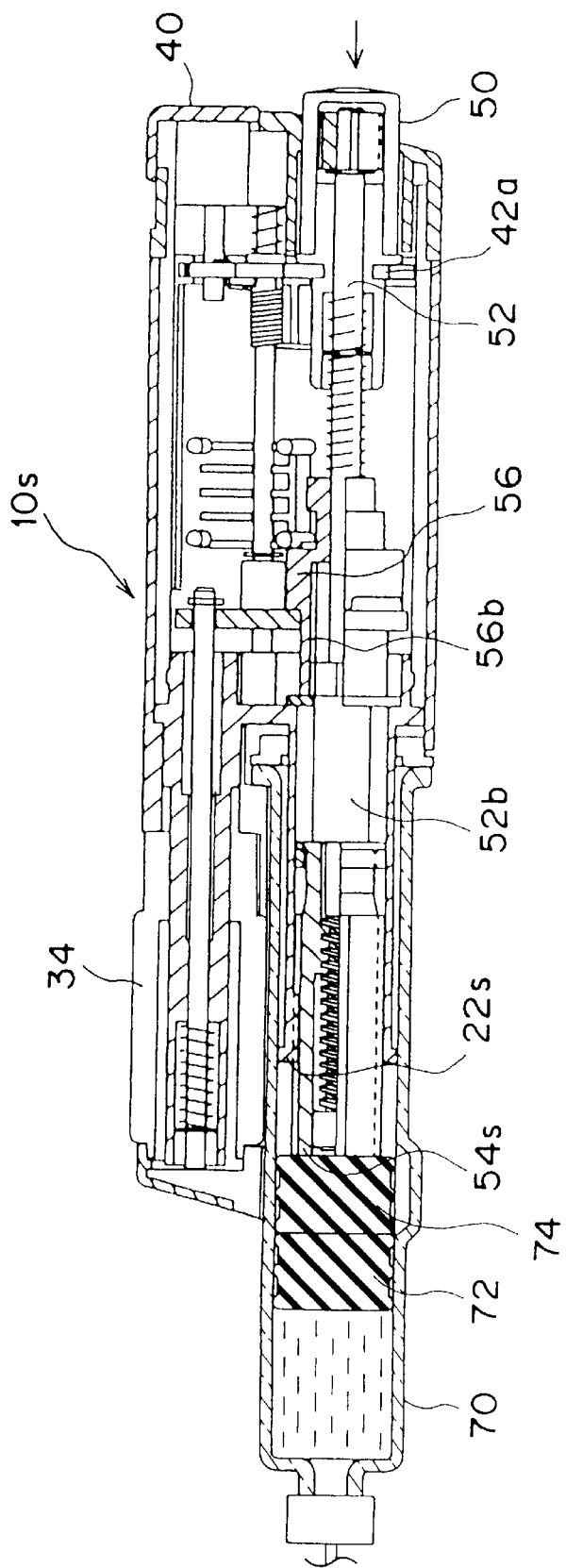
FIG. 18 is a sectional view showing the injection apparatus of FIGS. 15 and 16, and the state of the injection apparatus corresponds to the state III shown in FIG. 2C.

As shown in FIG. 18 corresponding to the state III of FIG. 2C, in order to release air completely from the syringe 77, the piston rod 54s is moved forward to press the piston rods 72 and 74 forward by pushing the operation knob 50 forward. That is, similarly to the first embodiment, the screw rod 52 moves together with the piston rod 54s from the initial position to the pressing position. That is, the screw rod 52 moves forward until the stopper strip 42a engages the stopper groove 50c of the operation knob 50, while the spline shaft part 52b of the screw rod 52 moves axially in engagement with the spline part 56b of the ratchet 56.

At this time, because the frictional force Fo between the stopper ring 54ms and the guide sleeve 22s is greater than the frictional force Fi between the stopper ring 54ms and the piston rod 54s as shown by the expression (1), the stopper ring 54ms keeps stationary with respect to the guide sleeve 22, while the piston rod 54s moves in sliding contact with the stopper ring 54ms. When the step 54ws of the groove of the piston rod 54s reaches the rear end surface of the stopper ring 54ms, the stopper ring 54ms is pressed by the step 54ws of the groove of the piston rod 54s, thus moving in sliding contact with the inner peripheral surface of the guide sleeve 22s. This is because the force of pressing the piston rod 54s forward is greater than the frictional force Fo between the stopper ring 54ms and the guide sleeve 22s.

Figure 19:
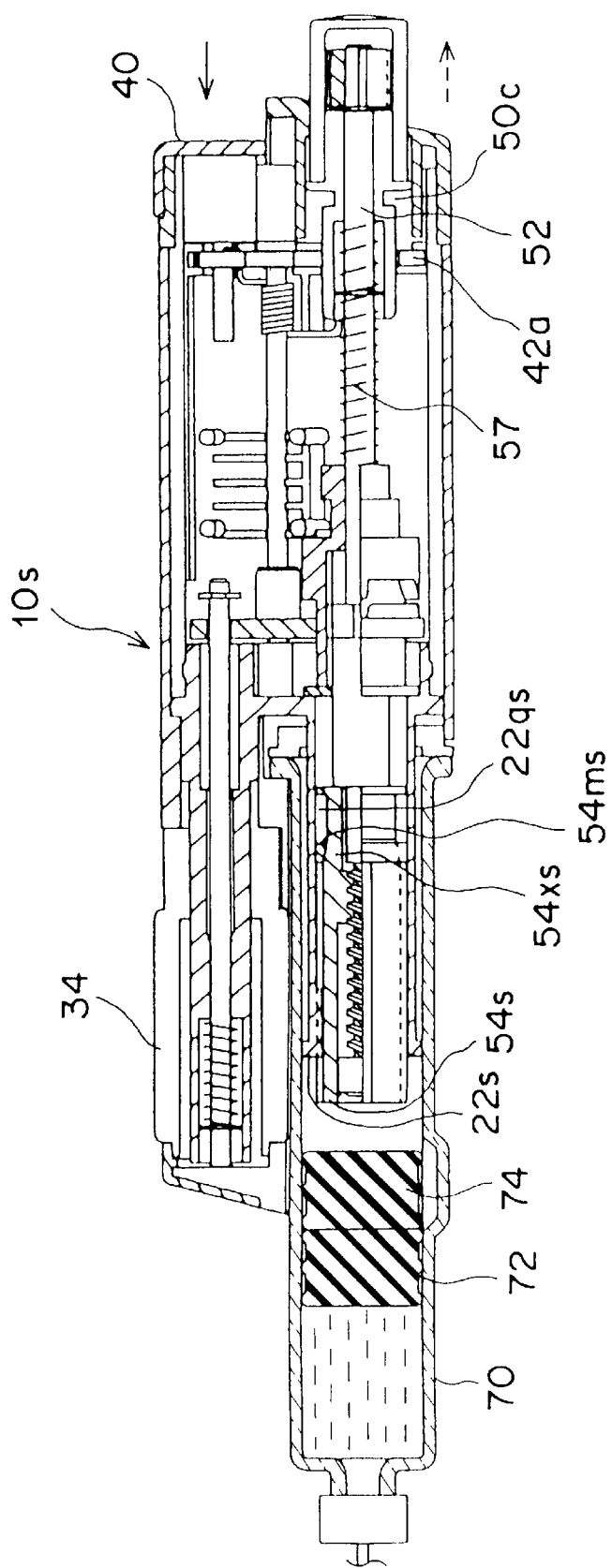
FIG. 19 is a sectional view showing the injection apparatus of FIGS. 15 and 16, and the state of the injection apparatus corresponds to the state IV shown in FIG. 2D.

Then, as shown in FIG. 19 corresponding to the state IV of FIG. 2D, the release button 40 is pressed to return the screw rod 52 and the piston rod 54s to the initial position. That is, similarly to the first embodiment, the stopper strip 42a is unlocked from the stopper groove 50c of the operation knob 50, and the screw rod 52 and the piston rod 54s are urged toward the initial position by the return force (P) of the return spring 57.

At this time, based on the condition of the expression (2), the stopper ring 54ms keeps stationary with respect to the guide sleeve 22s, and the piston rod 54s moves in sliding contact with the inner peripheral surface of the stopper ring 54ms. When the tapered part 54xs of the piston rod 54s reaches the stopper ring 54ms, the stopper ring 54ms fits in a wedge-shaped space located between the tapered part 54xs and the rear inner peripheral surface 22qs of the guide sleeve 22s. Consequently, the piston rod 54s is prevented from moving further, and the return of the screw rod 52 and the piston rod to the initial position is completed.

Similarly to the first embodiment, the return of the screw rod and the piston rod to the initial position is detected by a stopper position detector (not shown) for detecting the position of the stopper plate 42. The setting of the ampule 70 is completed with this state. At the same time, the indicator 61 displays the initial value 0.0 upon receipt of signals outputted from the stopper position detector.

Figure 20:
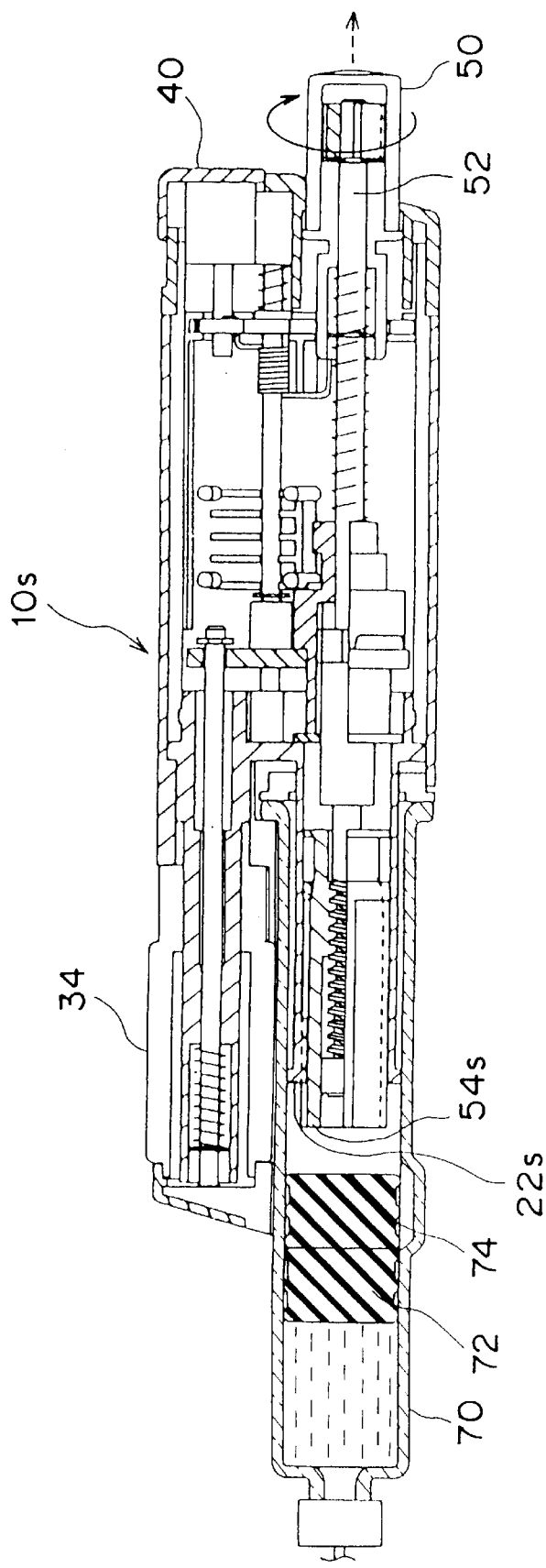
FIG. 20 is a sectional view showing the injection apparatus of FIGS. 15 and 16, and the state of the injection apparatus corresponds to the state V shown in FIG. 3A.

In order to set an injection amount, the operation knob 50 is rotated in a predetermined direction, as shown in FIG. 20 corresponding to the state V shown in FIG. 3A.

At this time, the stopper ring 54ms which has fitted in the tapered part 54xs prevents the piston rod 54s from moving axially. Therefore, upon rotation of the operation knob 50, the screw rod 52 is fed rearward with respect to the piston rod 54s and thus the total length of the piston rod 54s and the screw rod 52 becomes longer. That is, in this point, the second embodiment is different from the first embodiment in which the piston rod 54 is fed forward with respect to the screw rod 52.

The second embodiment is similar to the first embodiment in other points. The amount of the movement thereof corresponds to an injection amount, and a set injection amount is displayed by the indicator 61. The operation knob 50 can be rotated in only a direction in which the injection amount can be set by the ratchet mechanism.

Figure 21:
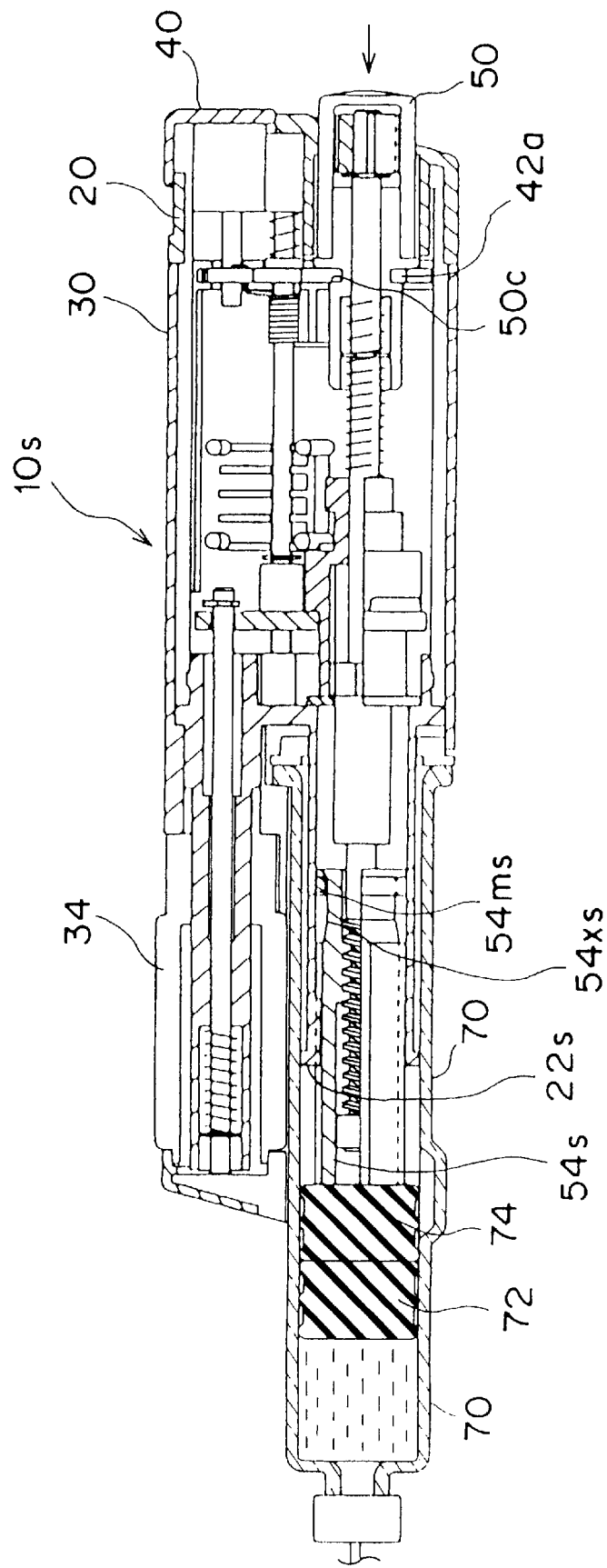
FIG. 21 is a sectional view showing the injection apparatus of FIGS. 15 and 16, and the state of the injection apparatus corresponds to the state VI shown in FIG. 3B.

After the injection amount is set, as shown in FIG. 21 corresponding to the state VI shown in FIG. 3B, an injection is given to a patient by pressing the operation knob 50 forward after the patient is pricked with the needle, similarly to the first embodiment. At this time, the screw rod 52 is pushed in up to a predetermined position at which the stopper strip 42a engages the stopper groove 50c of the screw rod 52. The distance between the stopper groove 50c of the screw rod 52 and the front end of the piston rod 54s at which the piston rod 54s contacts the piston 74 is increased by an amount corresponding to the rotation amount of the operation knob 50. Thus, the pistons 72 and 74 are pushed forward in correspondence to the extending amount thereof, thus giving an injection of the set amount to the patient. The stopper ring 54ms moves in the groove of the piston rod 54s between the tapered part 54xs thereof and the step 54ws thereof. Normally, the above extending amount of the length, of the screw rod 52 and the piston rod 54s, set by the operation knob 50 is greater than the stroke of the stopper ring 54rms, namely, the distance covered by the relative movement of the stopper strip 42a to the piston rod 54s between the tapered part 54xs and the step 54ws thereof. Therefore, for every injection, the stopper ring 54ms is pushed by the step 54ws of the groove of the piston rod 54s, thus moving forward along the inner peripheral surface of the guide sleeve 22s.

When injections are repeated, the release button 40 is pressed to return the screw rod 52 and the piston rod 54s to the initial position, and the above-described procedure is repeatedly performed. While injections are repeated in the above-described procedure, the stopper ring 54ms moves forward only, and does not move rearward. Accordingly, as injections are repeated, the initial position of the piston rod 54s and that of the stopper ring 54ms move forward.

When the ampule 70 is removed from the injection apparatus 10s, the screw rod 52 is returned to the initial position, and then, the operation knob 50 is forcibly moved rearward to move the piston rod 54s and the stopper ring 54ms rearward.

At this time, because the frictional force Fo between the stopper ring 54ms and the guide sleeve 22s is smaller than the pullback force (T) by which the screw rod is forcibly pulled back, the stopper ring 54ms which reaches the tapered part 54xs of the piston rod 54s moves rearward together with the piston rod 54s, with the stopper ring 54ms moving in sliding contact with the rear inner peripheral surface 22qs of the guide sleeve 22s.

When the rear end of the spline shaft part 52b of the screw rod 52 contacts the bottom surface 56e (see FIG. 16) of the rear end of the spline part 56b of the ratchet 56, the movement of the stopper ring 54ms is completed.

Then, the screw rod 52 is screwed on the piston rod 54s to shorten the total length of the screw rod 52 and the piston rod 54s by rotating the operation knob 50 reversely. In a normal operation, the screw rod 52 cannot be rotated reversely; however, at this time, the release button 40 is pressed deep to allow its reverse rotation, similarly to the first embodiment. Because the stopper ring 54ms prevents the piston rod 54s from moving axially, the screw rod 52 is moved forward by rotating the operation knob 50 reversely.

After the screw rod 52 is screwed on the piston rod 54s completely, similarly to the first embodiment, the operation knob 34 is rotated reversely to return the movable section 30 to the ampule insertion position, and then the ampule 70 is removed from the injection apparatus 10s.

According to the injection apparatus 10s of the second embodiment, when an injection amount is set, the screw rod 52 is fed rearward. Accordingly, the injection amount can be ascertained by the feeding amount of the screw rod 52, namely, that of the operation knob 50, in addition to the numerical display shown by the indicator 61.

The present invention is not limited to the above-described embodiment, but may be embodied in various other modes. For example, the driving means for moving the movable section relative to the body section may be constituted by a rack and a pinion.

It is claimed:

1. An injection apparatus, comprising an ampule having a piston for sealing an agent in a syringe, comprising:

piston rod means for pressing the piston of the ampule in an axial direction;

an ampule holding part having an ampule insertion outer opening, having an original circumference, which opening is expanded circumferentially when the ampule is inserted into the opening and having an ampule insertion space for inserting the ampule thereinto, wherein the outer opening is restored to its original circumference after the ampule is inserted into the ampule insertion space, so that the ampule is held by the ampule holding part temporarily; and ampule gripping means for gripping the ampule and preventing axial movement thereof.

2. The injection apparatus according to claim 1, wherein the ampule holding part has a pair of ampule-gripping elastic blades for securing the inserted ampule therebetween; the opening is defined between side edges of the pair of ampule-gripping elastic blades and between front edges thereof; the ampule insertion space is defined by an inner peripheral surface of the pair of ampule-gripping elastic blades; and the distance between the side edges of the pair of ampule-gripping elastic blades is shorter than an outer diameter of the syringe of the ampule.

3. The injection apparatus according to claim 1, which further comprises a body section which abuts the ampule and which contains the piston rod means and a movable section having the ampule holding part, wherein the body section and the movable section have driving means that allows the body section and the movable section to move relative to each other between an ampule insertion position at which the ampule is inserted into the ampule holding part of the movable section and a setting position at which the movable section is closest to the body section.

4. The injection apparatus according to claim 3, wherein the driving means comprises screw feeding means which has a guide screw shaft on the body section and a nut-type operation knob mounted on the movable section such that the operation knob is unmovable in the axial direction thereof, rotateable, and screws on a periphery of the guide screw shaft.

5. The injection apparatus according to claim 3, wherein the ampule has a flange, and wherein the ampule-gripping means comprises:

a flange hold-down part formed at a predetermined position of the ampule insertion space of the movable section, contacting a front surface of the flange of the inserted ampule, and moving the ampule rearward by pressing the front surface of the flange of the ampule when the movable section moves to the setting position, and a flange pressing part which is provided on the body section around the piston rod means and which is pressed against a rear surface of the flange of the ampule when the movable section and the body section are set at the setting position.

6. The injection apparatus according to claim 5, wherein the flange pressing part comprises:

a spacer which freely engages the periphery of the piston rod means, and which is placed at a predetermined position of the ampule insertion space when the movable section is located at the ampule insertion position so that the spacer substantially contacts the rear surface of the flange of the ampule; and an elastic O-ring provided at a predetermined position of the periphery of the piston road means such that the elastic O-ring is axially unmovable and pressed against a rear surface of the spacer when the movable section is located at the setting position.

7. The injection apparatus according to claim 3, wherein the piston rod means comprises:

a guide sleeve which is fixed to the body section, projects forward from the body section, is concentric with the inserted ampule, and has an outer diameter generally equal to an inner diameter of the syringe of the ampule;

a piston rod which is inserted into the guide sleeve such that the piston road is nonrotateable with respect to the guide sleeve and axially slideable, and which has a screw hole; and a screw rod which has a screw part, formed at a front end thereof, and screwing on a screw part in a form of a screw hole of the piston rod, and which has an operation knob formed at a rear end thereof, wherein the screw rod is movable together with the piston rod between an initial position and a pushing-in position.

8. The injection apparatus according to claim 7, wherein the piston rod means further comprises rotation regulation means for regulating the rotational direction of the screw rod in one direction.

9. The injection apparatus according to claim 8, which further comprises:

detection means for detecting the rotational amount of the screw rod of the piston rod means and detecting a return of the screw rod from the pushing-in position to the initial position;

display means for displaying the injection amount in correspondence to the rotational amount of the screw rod of the piston rod means after the screw rod returns to the initial position; and a rotation regulation release means for releasing the rotation regulation means of the piston rod means when the ampule is removed from the ampule insertion space.

10. The injection apparatus according to claim 7, wherein a concave part is formed on a peripheral surface of the piston rod, wherein the concave part comprises a bottom surface generally parallel with an inner peripheral surface of the guide sleeve, a front step surface being provided on a front side of the bottom surface and extending from the bottom surface outwardly in a radial direction of the piston rod, and a rear step surface being provided on a rear side of the bottom surface and extending from the bottom surface outwardly in the radial direction of the piston rod, and wherein the piston rod means further comprises:

spring means for automatically returning the screw rod and the piston rod to the initial position when a force for pushing in the screw rod and the piston rod is released, and a stopper member which is positioned in the concave of the piston rod, slides in contact with the bottom surface of the piston rod and the inner peripheral surface of the guide sleeve with a predetermined frictional force, moves together with the piston rod with the stopper member in contact with the rear step surface of the piston rod when the piston rod is pushed in, and stops the movement of the piston rod with the stopper member in contact with the front step surface of the piston rod when the piston rod is returned by the spring means, wherein a frictional force between the stopper member and the bottom surface of the piston rod is smaller than an automatic return force of the spring means; and a frictional force between the stopper member and the inner peripheral surface of the guide sleeve is greater than the automatic return force of the spring means.

11. The injection apparatus according to claim 8, wherein a concave part is formed a peripheral surface of the piston rod, wherein the concave part comprises a bottom surface generally parallel with an inner peripheral surface of the guide sleeve, a front step surface being provided on a front side of the bottom surface and extending from the bottom surface outwardly in a radial direction of the piston rod, and a rear step surface being provided on a rear side of the bottom surface and extending from the bottom surface outwardly in the radial direction of the piston rod, and wherein the piston rod means further comprises:

spring means for automatically returning the screw rod and the piston rod to the initial position when a force for pushing in the screw rod and the piston rod is released, and a stopper member which is positioned in the concave of the piston rod, slides in contact with the bottom surface of the piston rod and the inner peripheral surface of the guide sleeve with a predetermined frictional force, moves together with the piston rod with the stopper member in contact with the rear step surface of the piston rod when the piston rod is pushed in, and stops the movement of the piston rod with the stopper member in contact with the front step surface of the piston rod when the piston rod is returned by the spring means, wherein a frictional force between the stopper member and the bottom surface of the piston rod is smaller than an automatic return force of the spring means; and a frictional force between the stopper member and the inner peripheral surface of the guide sleeve is greater than the automatic return force of the spring means.

12. The injection apparatus according to claim 9, wherein a concave part is formed on a peripheral surface of the piston rod, wherein the concave part comprises a bottom surface generally parallel with an inner peripheral surface of the guide sleeve, a front step surface being provided on a front side of the bottom surface and extending from the bottom surface outwardly in a radial direction of the piston rod, and a rear step surface being provided on a rear side of the bottom surface and extending from the bottom surface outwardly in the radial direction of the piston rod, and wherein the piston rod means further comprises:

spring means for automatically returning the screw rod and the piston rod to the initial position when a force for pushing in the screw rod and the piston rod is released, and a stopper member which is positioned in the concave of the piston rod, slides in contact with the bottom surface of the piston rod and the inner peripheral surface of the guide sleeve with a predetermined frictional force, moves together with the piston rod with the stopper member in contact with the rear step surface of the piston rod when the piston rod is pushed in, and stops the movement of the piston rod with the stopper member in contact with the front step surface of the piston rod when the piston rod is returned by the spring means, wherein a frictional force between the stopper member and the bottom surface of the piston rod is smaller than an automatic return force of the spring means; and a frictional force between the stopper member and the inner peripheral surface of the guide sleeve is greater than the automatic return force of the spring means.

13. The injection apparatus according to claim 10, wherein the stopper member is made of a frictional/elastic material such as a rubber, wherein the front step surface of the piston rod is an inclined surface which extends from the bottom surface outwardly in the radial direction and towards a front side of the piston rod, and wherein a wedge-shaped space is formed between the inclined surface and the inner peripheral surface of the guide sleeve.

14. The injection apparatus according to claim 11, wherein the stopper member is made of a frictional/elastic material such as a rubber, wherein the front step surface of the piston rod is an inclined surface which extends from the bottom surface outwardly in the radial direction and towards a front side of the piston rod, and wherein a wedge-shaped space is formed between the inclined surface and the inner peripheral surface of the guide sleeve.

15. The injection apparatus according to claim 12, wherein the stopper member is made of a frictional/elastic material such as a rubber, wherein the front step surface of the piston rod is an inclined surface which extends from the bottom surface outwardly in the radial direction and towards a front side of the piston rod, and wherein a wedge-shaped space is formed between the inclined surface and the inner peripheral surface of the guide sleeve.

16. The injection apparatus according to claim 10, wherein a stroke of the stopper member moving between the front step surface of the piston rod and the rear step surface thereof is smaller than the amount of the screw rod which is fed relative to the piston rod by rotating the screw rod to set a dosage amount for injection.

17. The injection apparatus according to claim 11, wherein a stroke of the stopper member moving between the front step surface of the piston rod and the rear step surface thereof is smaller than the amount of the screw rod which is fed relative to the piston rod by rotating the screw rod to set a dosage amount for injection.

18. The injection apparatus according to claim 12, wherein a stroke of the stopper member moving between the front step surface of the piston rod and the rear step surface thereof is smaller than the amount of the screw rod which is fed relative to the piston rod by rotating the screw rod to set a dosage amount for injection.

19. The injection apparatus according to claim 10, wherein the concave is formed as a circumferential concave, and the stopper member is a ring-shaped stopper member provided on the circumferential concave.

20. The injection apparatus according to claim 11, wherein the concave is formed as a circumferential concave, and the stopper member is a ring-shaped stopper member provided on the circumferential concave.

21. The injection apparatus according to claim 12, wherein the concave is formed as a circumferential concave, and the stopper member is a ring-shaped stopper member provided on the circumferential concave.

* * * * *

UNITED STATES PATENT AND TRADEMARK OFFICE
CERTIFICATE OF CORRECTION

PATENT : 5,823,998

DATED : October 20, 1998

INVENTOR(S) : Hideto Yamagata

It is certified that error appears in the above-identified patent and that said Letters Patent is hereby corrected as shown below:

Column 19, line 59 reads ..."road"... should read --rod--

Signed and Sealed this

Twenty-third Day of November, 1999

Attest:

Attesting Officer

Q. TODD DICKINSON

Acting Commissioner of Patents and Trademarks